(12) United States Patent
Tajima et al.

(10) Patent No.: US 7,323,456 B2
(45) Date of Patent: Jan. 29, 2008

(54) CARBOXYLIC ACID DERIVATIVES COMPOUNDS AND AGENTS COMPRISING THE COMPOUNDS AS ACTIVE INGREDIENT

(75) Inventors: Hisao Tajima, Mishima-gun (JP); Yoshisuke Nakayama, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 486 days.

(21) Appl. No.: 10/495,158

(22) PCT Filed: Nov. 11, 2002

(86) PCT No.: PCT/JP02/11729

§ 371 (c)(1),
(2), (4) Date: May 11, 2004

(87) PCT Pub. No.: WO03/042194

PCT Pub. Date: May 22, 2003

(65) Prior Publication Data

US 2004/0254370 A1   Dec. 16, 2004

(30) Foreign Application Priority Data

Nov. 12, 2001 (JP) .............................. 2001-346583

(51) Int. Cl.
*A61K 31/55* (2006.01)
*C07D 413/10* (2006.01)
*C07D 417/10* (2006.01)

(52) U.S. Cl. ..................... 514/212; 540/597; 540/603

(58) Field of Classification Search ................ 540/597, 540/603; 514/212
See application file for complete search history.

(56) References Cited

U.S. PATENT DOCUMENTS 5,466,687 A * 11/1995 Maier et al. ........... 514/217.05
6,180,660 B1 * 1/2001 Whitney et al. ............ 514/451
7,105,556 B2 * 9/2006 Cheng et al. ............... 514/374
2003/0092697 A1 * 5/2003 Cheng et al. ............ 514/210.2

FOREIGN PATENT DOCUMENTS

| EP | 1067109 A1 | 1/2001 |
| WO | WO 97/31907 A1 | 9/1997 |
| WO | WO 00/08002 A1 | 2/2000 |
| WO | WO 01/21602 A1 | 3/2001 |

OTHER PUBLICATIONS

Hart et al. "Preparation of substituted . . . " CA 138:287662 (2003).*
Fujiwara et al. "Troglitazone and . . . " Life Science v.67, pp. 2405-2416 (2000).*

* cited by examiner

*Primary Examiner*—Celia Chang
(74) *Attorney, Agent, or Firm*—Sughrue Mion, PLLC

(57) ABSTRACT

A compound of formula (I)

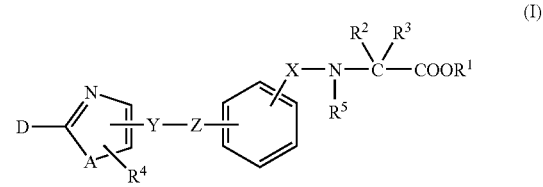

(wherein all symbols are as defined in the specification) and a salt thereof, and peroxisome proliferator activated receptor regulator comprising thereof as active ingredient. Because a compound of formula (I) have an activity of regulating peroxisome proliferator activated receptor regulator, the compound of formula (I) is useful as a hypoglycemic agent, a hypolipidemic agent, a preventive and/or treatment agent for diseases associating metabolic disorders (diabetes, obesity, syndrome X, hypercholesterolemia, hyperlipoproteinemia, etc.), hyperlipemia, atherosclerosis, hypertension, circulatory diseases, overeating, ischemic heart diseases, etc., an HDL cholesterol-elevating agent, an LDL cholesterol and/or VLDL cholesterol-lowering agent and a drug for relief from risk factors of diabetes or syndrome X.

7 Claims, No Drawings

CARBOXYLIC ACID DERIVATIVES COMPOUNDS AND AGENTS COMPRISING THE COMPOUNDS AS ACTIVE INGREDIENT

TECHNICAL FIELD

The present invention relates to carboxylic acid derivative compounds.

More specifically, the present invention relates to (1) a carboxylic acid derivative compound represented by formula (I)

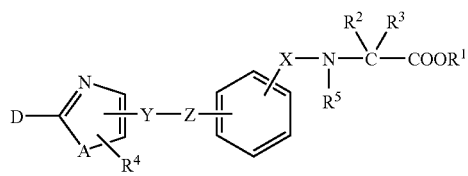

(wherein all symbols have the same meanings as described below), or a nontoxic salt thereof, (2) a process for preparing thereof, and (3) an agent comprising thereof as an active ingredient.

BACKGROUND ART

Recently in the study of transcription factors concerned with marker genes expression in adipocytes differentiation, peroxisome proliferator activated receptor (abbreviated as PPAR hereinafter), which is one of intranuclear receptors, has been focused. cDNAs of PPAR were cloned from various kinds of animals, and plural isoform genes were found, particularly in mammals three types of isoforms ($\alpha$, $\delta$, $\gamma$) are known (see *J. Steroid Biochem. Molec. Biol.*, 51, 157 (1994); *Gene Expression.*, 4, 281 (1995); *Biochem Biophys. Res. Commun.*, 224, 431 (1996); *Mol. Endocrinology.*, 6, 1634 (1992)). PPAR $\gamma$ isoform is predominantly expressed in adipose tissues, immune cells, adrenal gland, spleen, small intestine. PPAR $\alpha$ isoform is mainly expressed in adipose tissue, liver, retina, and PPAR $\delta$ isoform is widely expressed without specificity for tissue (see *Endocrinology.*, 137, 354 (1996)).

On the other hand, the following thiazolidine derivatives are known as agents for the treatment of non-insulin dependent diabetes mellitus (NIDDM) and are hypoglycemic agents which are used for the improvement of hyperglycemia in the patients suffering from diabetes. They are also effective for the improvement of hyperinsulinemia, glucose tolerance and decrease of serum lipid and therefore they are thought to be considerably hopeful as agents for the treatment of insulin resistance.

pioglitazone

-continued

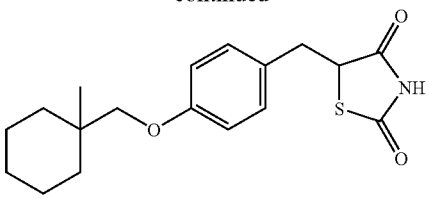

ciglitazone

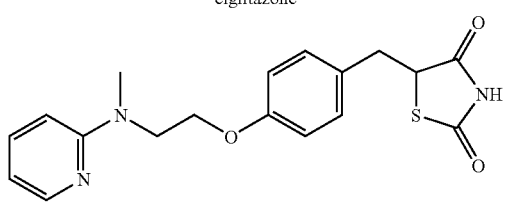

BRL49653

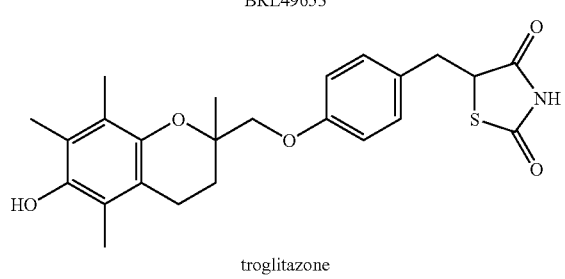

troglitazone

One of the target proteins in the cells of these thiazolidine derivatives is exactly PPAR $\gamma$ and it is resolved that they enhance the transcription activity of PPAR $\gamma$ (see *Endocrinology.*, 137, 4189 (1996); *Cell*, 83, 803 (1995); *Cell*, 83, 813 (1995); *J. Biol. Chem.*, 270, 12953 (1995)). Therefore, a PPAR $\gamma$ activator (agonist) which enhances its transcription activity is thought to be hopeful as a hypoglycemic agent and/or a hypolipidemic agent. Furthermore, since a PPAR $\gamma$ agonist is known to promote the expression of PPAR $\gamma$ protein itself (*Genes & Development*, 10, 974 (1996)), an agent which increases the expression of PPAR $\gamma$ protein itself as well as PPAR $\gamma$ activating agent is also thought to be clinically useful.

PPAR $\gamma$ is related to adipocytes differentiation (see *J. Biol. Chem.*, 272, 5637 (1997) and *Cell*, 83, 803 (1995)). It is known that thiazolidine derivatives which activate this receptor promote adipocytes differentiation. Recently it was reported that thiazolidine derivatives increase fat mass and cause man to gain weight and to become obese (see *Lancet.*, 349, 952 (1997)). Therefore, it is also thought that antagonists which inhibit PPAR $\gamma$ activity and agents that decrease the expression of PPAR $\gamma$ protein itself are also clinically applicable. On the other hand, a compound that phosphorylates PPAR $\gamma$ protein and decreases its activity is reported (*Science*, 274, 2100 (1996)). This implies that an agent which does not bind on PPAR $\gamma$ protein as a ligand, but inhibits its activity is also clinically applicable.

From these, PPAR $\gamma$ activators (agonists) and PPAR $\gamma$ regulators for its expression that can increase the expression of the protein itself are expected to be useful as hypoglycemic agents, hypolipidemic agents, and agents for prevention and/or treatment of diseases associated with metabolic disorders such as diabetes, obesity, syndrome X, hypercholesterolemia and hyperlipoproteinemia etc., hyperlipidemia, atherosclerosis, hypertension, circulatory diseases and overeating etc.

On the other hand, antagonists that inhibit the transcription activity of PPAR γ or PPAR γ regulators that inhibit the expression of the protein itself are expected to be useful as hypoglycemic agents and agents for prevention and/or treatment of diseases associated with metabolic disorders such as diabetes, obesity and syndrome X etc., hyperlipidemia, atherosclerosis, hypertension and overeating etc.

The following fibrate compound (e.g. chlofibrate) is known as a hypolipidemic agent.

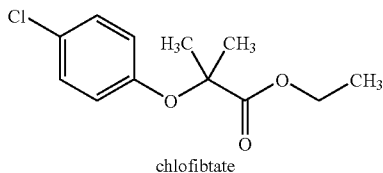

chlofibtate

And, it is also resolved that one of the target proteins in the cells of fibrate compounds is PPAR α (see *Nature*, 347, 645 (1990); *J. Steroid Biochem. Molec. Biol.*, 51, 157 (1994); *Biochemistry*, 32, 5598 (1993)). From these facts, PPAR α regulators which can be activated by fibrate compounds are thought to have a hypolipidemic effect, and so they are expected to be useful as agents for prevention and/or treatment of hyperlipidemia etc.

Besides, it has been recently reported that PPAR α possesses anti-obese activity in the specification of WO 9736579. In addition, it was reported that the elevation of high density lipoprotein (HDL) cholesterol level and the reduction of low density lipoprotein (LDL) cholesterol, very low density lipoprotein (VLDL) cholesterol and triglyceride levels were induced by activation of PPAR α (*J. Lipid Res.*, 39, 17 (1998)). It was also reported that composition of fatty acids in blood, hypertension and insulin resistance were improved by administration of bezafibrate which is one of fibrate compounds (*Diabetes*, 46, 348 (1997)). Therefore, agonists that activate PPAR α and PPAR α regulators that promote expression of PPAR α protein itself are useful as hypolipidemic agents and agents for treatment of hyperlipidemia, and are expected to have HDL cholesterol level-elevating effect, LDL cholesterol and/or VLDL cholesterol levels-lowering effect, inhibition on the progress of atherosclerosis and anti-obese effect. Therefore, they are thought to be hopeful agents for the treatment and/or prevention of diabetes as hypoglycemic agents, for the improvement of hypertension, for the relief from risk factor of syndrome X and for the prevention of occurrence of ischemic coronary diseases.

On the other hand, few reports are found on ligands that activate PPAR δ significantly or on biological activities associated with PPAR δ.

PPAR δ is sometimes called PPAR β, or it is also called NUC1 in human. Until now, as for activity of PPAR δ, it is disclosed in the specification of WO 9601430 that hNUC1B (PPAR subtype whose structure is different from that of human NUC1 in one amino acid) inhibited the transcription activities of human PPAR α and thyroid hormone receptor. Recently in the specification of WO 9728149, it was reported that the compounds, which possessed high affinity to PPAR δ protein and which could activate PPAR δ significantly (i.e. agonists) were found out and that they had HDL (high density lipoprotein) cholesterol level-elevating activity. Therefore, agonists that can activate PPAR δ are expected to have HDL cholesterol level-elevating effect, and so they are expected to be useful for the inhibition on the progress of atherosclerosis and treatment thereof, as hypolipidemic agents and hypoglycemic agents, for the treatment of hyperlipidemia, as hypoglycemic agents, for the treatment of diabetes, for the relief from risk factor of syndrome X, and for the prevention of occurrence of ischemic heart diseases.

BACKGROUND ART

In the specification of WO01/21602, it is described that oxa and thiazole derivatives of formula (A)

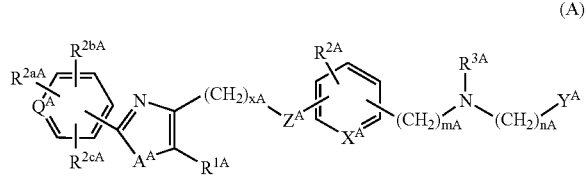

(A)

(wherein $X^A$ is 1, 2, 3 or 4, mA is 1 or 2, n is 1 or 2, $Q^A$ is C or N, $A^A$ is O or S, $Z^A$ is O or a bond, $R^{1A}$ is hydrogen atom or alkyl, $X^A$ is CH or N, $R^{2A}$ is H, alkyl etc., $R^{2aA}$, $R^{2bA}$ and $R^{2cA}$ are hydrogen atom, alkyl, alkoxy, halogen atom, amino or substituted amino (substituted amino is amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl. In addition, the amino substituednts may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl (optionally substituted with alkyl, alkoxy, alkylthio, halo, trifluoromethyl, hydroxyl.), $R^{3A}$ is H, alkyl, arylalkyl etc., Y is $CO_2R^{4A}$ ($R^{4A}$ is hydrogen atom, alkyl etc.) etc.) and pharmaceutically acceptable salts thereof are useful as antidiabetic and antiobesity agents.

DISCLOSURE OF THE INVENTION

In order to find a compound having a PPAR modulating activity, the present inventors have conducted intensive studies and found, as a result, that the objects can be accomplished by the compound represented by formula (I), and thus the present invention has been accomplished.

The present invention relates to (1) a carboxylic acid derivative compound represented by formula (I)

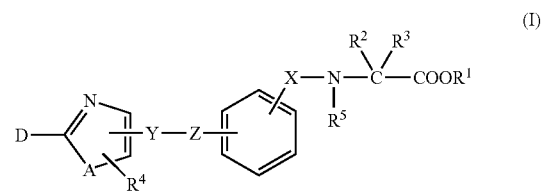

(I)

(wherein X and Y are each independently C1-4 alkylene, Z is —O— or —S—, $R^1$, $R^2$, $R^3$ and $R^4$ are each independently hydrogen atom, or C1-8 alky,
$R^5$ is C2-8 alkenyl,
A is —O— or —S—,
D is $D^1$, $D^2$, $D^3$, $D^4$, or $D^5$,
$D^1$ is C1-8 alkyl,
$D^2$ is

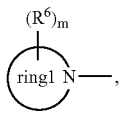

ring1 is saturated 3-7 membered mono-hetero aryl containing one nitrogen atom and optionally another one hetero atom selected from oxygen, sulfur and nitrogen atoms,
$D^3$ is

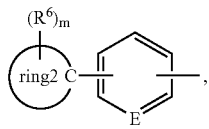

ring2 is
(1) optionally partially or fully saturated C3-10 mono- or bi-carbocyclic aryl, or
(2) optionally partially or fully saturated 3-10 membered mono- or bi-hetero aryl containing 1-4 hetero atoms selected from oxygen, nitrogen and sulfur atom,
$D^4$ is

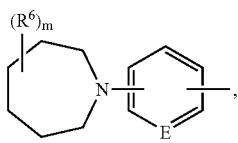

$D^5$ is

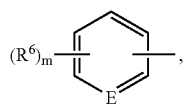

$R^6$ is (1) hydrogen atom, (2) C1-8 alkyl, (3) C1-8 alkoxy, (4) $CF_3$, (5) $OCF_3$, (6) halogen atom, (7) nitro, or (8) $NR^7R^8$,
$R^7$ or $R^8$ is hydrogen atom, or C1-8 alkyl, or
$R^7$ and $R^8$, taken together with the nitrogen atom to which they are attached, form saturated 3-7 membered mono-hetero aryl containing one nitrogen atom and optionally another one hetero atom selected from oxygen, sulfur and nitrogen atom, and the saturated hetero aryl is optionally substituted with C1-8 alkyl,
E is CH or nitrogen atom, and
m is integer of 1-3.)
or a nontoxic salt thereof,
(2) a process for preparing thereof, and
(3) an agent comprising thereof as an active ingredient.

In the specification, C1-8 alkyl means methyl, ethyl, propyl, butyl, pentyl, hexyl, heptyl, octyl or isomeric groups thereof.
In the specification, C2-8 alkenyl means ethenyl, propenyl, butenyl, pentenyl, hexenyl, heptenyl, octenyl or isomeric groups thereof.
In the specification, C1-8 alkoxy means methoxy, ethoxy, propoxy, butoxy, pentyloxy, hexyloxy, heptyloxy, octyloxy or isomeric groups thereof.
In the specification, C1-4 alkylene means methylene, ethylene, trimethylene, tetramethylene or isomeric groups thereof.
In the specification, halogen is chlorine, bromine, fluorine or iodine.
In the specification, saturated 3-7 membered mono-hetero aryl containing one nitrogen atom and optionally another one hetero atom selected from oxygen, sulfur and nitrogen atom represented by ring 1 is, for example, aziridine, azetidine, pyrrolidine, imidazolidine, pyrazolidine, piperidine, piperazine, perhydropyrimidine, perhydropyridazine, perhydroazepine, perhydrodiazepine, tetrahydrooxazole (oxazolidine), tetrahydroisoxazole (isoxazolidine), tetrahydrothiazole (thiazolidine), tetrahydroisothiazole (isothiazolidine), tetrahydrooxazine, perhydrooxazepine, tetrahydrothiazine, perhydrothiazepine, morpholine, thiomorpholine etc.
In the specification, saturated 3-6 membered mono-hetero aryl containing one nitrogen atom and optionally another one hetero atom selected from oxygen, sulfur and nitrogen atom, represented by $R^6$ and $R^7$, taken together with the nitrogen atom to which they are attached, is, for example, aziridine, azetidine, pyrrolidine, imidazolidine, pyrazolidine, piperidine, piperazine, perhydropyrimidine, perhydropyridazine, tetrahydrooxazole (oxazolidine), tetrahydroisoxazole (isoxazolidine), tetrahydrothiazole (thiazolidine), tetrahydroisothiazole (isothiazolidine), tetrahydrooxazine, tetrahydrothiazine, morpholine, thiomorpholine etc.
In the specification, partially or fully optionally saturated C3-10 mono- or bi-carbocyclic aryl is, for example, cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclooctene, cyclopentadiene, cyclohexadiene, cycloheptadiene, cyclooctadiene, benzene, pentalene, azulene, perhydroazulene, perhydropentalene, indene, perhydroindene, indan, naphthalene, teterahydronaphthalene or perhydronaphthalene etc.
In the specification, among partially or fully optionally saturated 3-10 membered mono- or bi-hetero aryl containing 1-4 hetero atoms selected from oxygen, nitrogen or sulfur atom represented by ring2, 3-10 membered mono- or bi-hetero aryl containing 1-4 hetero atoms selected from oxygen, nitrogen or sulfur atom means, for example, pyrrole, imidazole, triazole, tetrazole, pyrazole, pyridine, pyrazine, pyrimidine, pyridazine, azepine, diazepine, furan, pyran, oxepine, thiophene, thiaine, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole etc.
Also, partially or fully saturated 3-10 membered mono- or bi-hetero aryl containing 1-4 hetero atoms selected from oxygen, nitrogen or sulfur atom, means, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyrazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiaine (dihydrothiopyran), tetrahydrothiaine (tetrahydrothiopyran), dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dithiolane, dithiane, dioxaindan, benzodioxane, chroman, benzodithiolane, benzodithiane etc.

Unless otherwise specified, all isomers are included in the present invention. For example, alkyl, alkoxy and alkylene group includes straight or branched ones. In addition, isomers on double bond, ring, fused ring (E-, Z-, cis-, trans-isomer) isomers generated from asymmetric carbon atom(s) (R-, S-, α-, β-isomer, enantiomer, diastereomer), optically active isomers (D-, L-, d-, I-isomer), polar compounds generated by chromatographic separation (more polar compound, less polar compound), equilibrium compounds, rotamer, mixtures thereof at voluntary ratios and racemic mixtures are also included in the present invention.

According to the present invention, unless otherwise indicated and as is apparent for those skilled in the art, symbol ......

indicates that it is bound to the opposite side of the sheet (namely α-configuration), symbol ◢ indicates that it is bound to the front side of the sheet (namely β-configuration), symbol ⌇⌇ indicates that it is α-, β- or a mixture thereof, and symbol

▬▬▬ indicates that it is a mixture of α-configuration and β-configuration.

The compound of the present invention can be converted into a nontoxic salt by known methods.

A nontoxic salt is preferably pharmaceutically acceptable and water-soluble.

A nontoxic salt means, for example, salts of alkali metals (potassium, sodium, lithium, etc.), salts of alkaline earth metals (calcium, magnesium, etc.), ammonium salts (tetramethylammonium, tetrabutylammonium, etc.), salts of organic amines (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid-addition salts (inorganic acid salts (hydrochloride, hydrobromate, hydroiodate, sulfate, phosphate, nitrate, etc.), organic acid salts (acetate, trifluoroacetate, lactate, tartrate, oxalate, fumarate, maleate, benzoate, citrate, methane sulfonate, ethane sulfonate, benzene sulfonate, toluene sulfonate, isethionate, glucuronate, gluconate, etc.), etc.

Furthermore, solvates of compounds of the present invention, and the above alkai (earth) metals, ammonium, organic amines and acid-addition salts thereof, is included in the present invention.

The solvate is preferably nontoxic and water-soluble. Appropriate solvates means, for example, solvates such as water, an alcohol solvent (ethanol etc.), etc.

In the present invention, PPAR regulator includes all the regulators of PPAR α, γ, δ, α+γ, α+δ, γ+δ and α+γ+δ. Preferable regulatory fashion is, PPAR α regulator, PPAR γ regulator, PPAR δ regulator, PPAR α+γ regulator, PPAR α+δ regulator, more preferably PPAR α+γ regulator.

PPAR regulator also includes PPAR agonist and PPAR antagonist. PPAR regulator is preferably PPAR agonist, more preferably PPAR α agonist, PPAR γ agonist, PPAR δ agonist, PPAR α+γ agonist or PPAR α+δ agonist, particularly preferably PPAR α+γ agonist.

In the specification, $R^5$ is preferably propenyl, and more preferably allyl.

In the specification, X is preferably C1-2 alkylene (methylene, ethylene), and more preferably methylene.

In the specification, Y is preferably C1-2 alkylene (methylene, ethylene), and more preferably ethylene.

In the specification, Z is preferably —O— or —S—, and more preferably —O—.

In the specification, A is preferably —O— or —S—, and more preferably —O—.

In the specification, D is preferably $D^1$, $D^2$, $D^3$ or $D^4$, and more preferably $D^3$ or $D^4$, and most preferably $D^4$.

Among the compounds represented by formula (I), preferred compounds are compounds represented by formula (I-A)

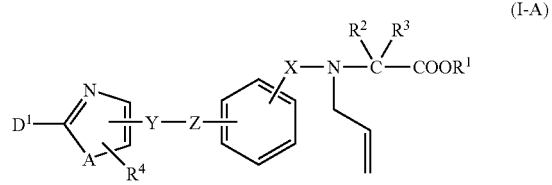

(I-A)

(wherein all symbols have the same meanings as described above.), compounds represented by formula (I-B)

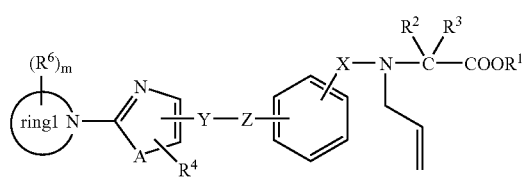

(I-B)

(wherein all symbols have the same meanings as described above.), compounds represented by formula (I-C)

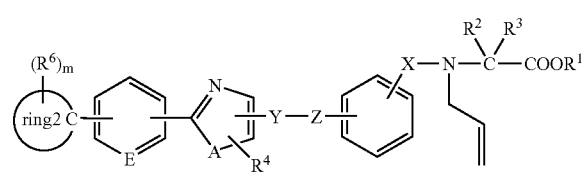

(I-C)

(wherein all symbols have the same meanings as described above.), compounds represented by formula (I-D)

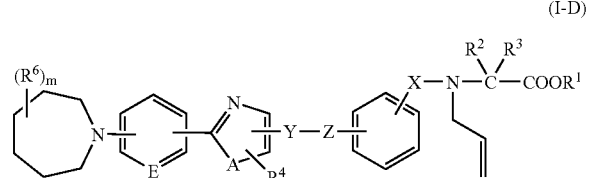

(I-D)

(wherein all symbols have the same meanings as described above.), and compounds represented by formula (I-E)

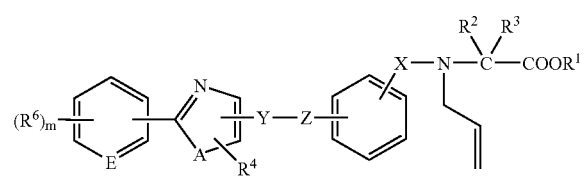

(I-E)

(wherein all symbols have the same meanings as described above.).

Concrete compounds of the present invention include compounds shown in Tables 1 to 5, compounds described in Examples, and nontoxic salts thereof.

In each Table, Me represents methyl group, Et represents ethyl group, Pr represents propyl group, i-Pr represents isopropyl group, t-Bu represents tertiarybutyl group, and other symbols have the same meanings as described above.

TABLE 1

(I-A-1)

| No. | $D^1$ | A | Z |
|---|---|---|---|
| 1 | Me | —O— | —O— |
| 2 | Et | —O— | —O— |
| 3 | Pr | —O— | —O— |
| 4 | i-Pr | —O— | —O— |
| 5 | t-Bu | —O— | —O— |
| 6 | Me | —O— | —S— |
| 7 | Et | —O— | —S— |
| 8 | Pr | —O— | —S— |
| 9 | i-Pr | —O— | —S— |
| 10 | t-Bu | —O— | —S— |
| 11 | Me | —S— | —O— |
| 12 | Et | —S— | —O— |
| 13 | Pr | —S— | —O— |
| 14 | i-Pr | —S— | —O— |
| 15 | t-Bu | —S— | —O— |
| 16 | Me | —S— | —S— |
| 17 | Et | —S— | —S— |
| 18 | Pr | —S— | —S— |
| 19 | i-Pr | —S— | —S— |
| 20 | t-Bu | —S— | —S— |

TABLE 2

(I-B-1)

| No. | $R^6$—ring1 N— | A | Z |
|---|---|---|---|
| 1 | pyrrolidine | —O— | —O— |
| 2 | piperidine | —O— | —O— |
| 3 | azepane | —O— | —O— |
| 4 | Me—N-piperazine | —O— | —O— |

TABLE 2-continued (I-B-1)

Structure: ring1(R⁶)N—[imidazole with A, Me]—CH₂CH₂—Z—[phenyl]—CH₂—N(allyl)—CH₂COOH

| No. | ring1(R⁶)N— | A | Z |
|---|---|---|---|
| 5 | morpholine-N— | —O— | —O— |
| 6 | pyrrolidine-N— | —O— | —S— |
| 7 | piperidine-N— | —O— | —S— |
| 8 | azepane-N— | —O— | —S— |
| 9 | Me-N(piperazine)N— | —O— | —S— |
| 10 | morpholine-N— | —O— | —S— |
| 11 | pyrrolidine-N— | —S— | —O— |
| 12 | piperidine-N— | —S— | —O— |
| 13 | azepane-N— | —S— | —O— |
| 14 | Me-N(piperazine)N— | —S— | —O— |
| 15 | morpholine-N— | —S— | —O— |
| 16 | pyrrolidine-N— | —S— | —S— |
| 17 | piperidine-N— | —S— | —S— |
| 18 | azepane-N— | —S— | —S— |
| 19 | Me-N(piperazine)N— | —S— | —S— |
| 20 | morpholine-N— | —S— | —S— |

TABLE 3
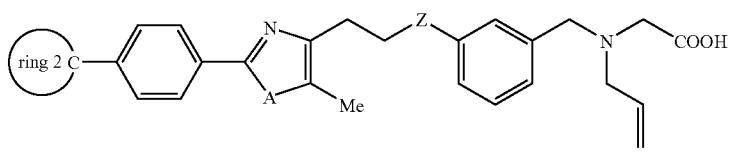
(I-C-1)
| No. | ring2 C— | A | Z |
|---|---|---|---|
| 1 | phenyl | —O— | —O— |
| 2 | cyclohexyl | —O— | —O— |
| 3 | tetrahydropyran-4-yl | —O— | —O— |
| 4 | 1,2,3-thiadiazol-4-yl | —O— | —O— |
| 5 | phenyl | —O— | —S— |
| 6 | cyclohexyl | —O— | —S— |
| 7 | tetrahydropyran-4-yl | —O— | —S— |
| 8 | 1,2,3-thiadiazol-4-yl | —O— | —S— |
| 9 | phenyl | —S— | —O— |
| 10 | cyclohexyl | —S— | —O— |
| 11 | tetrahydropyran-4-yl | —S— | —O— |
| 12 | 1,2,3-thiadiazol-4-yl | —S— | —O— |
| 13 | phenyl | —S— | —S— |

TABLE 3-continued
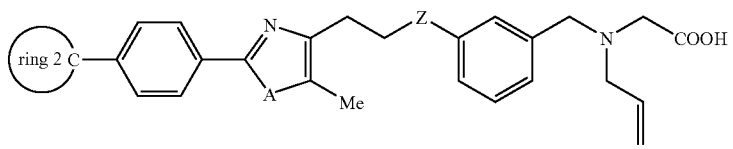
(I-C-1)
| No. | ring2 C— | A | Z |
|-----|----------|----|----|
| 14 | cyclohexyl | —S— | —S— |
| 15 | tetrahydropyran-4-yl | —S— | —S— |
| 16 | 1,2,3-thiadiazol-4-yl | —S— | —S— |
TABLE 4
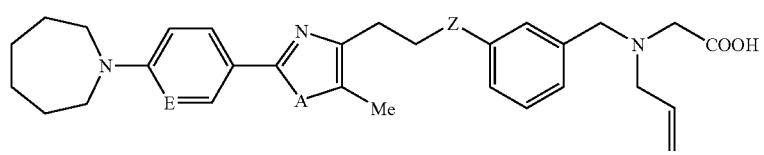
(I-D-1)
| No. | E | A | Z |
|-----|-----|-----|-----|
| 1 | —CH= | —O— | —O— |
| 2 | —N= | —O— | —O— |
| 3 | —CH= | —O— | —S— |
| 4 | —N= | —O— | —S— |
| 5 | —CH= | —S— | —O— |
| 6 | —N= | —S— | —O— |
| 7 | —CH= | —S— | —S— |
| 8 | —N= | —S— | —S— |

TABLE 5

(I-E-1)

| No. | E | R⁶ | A | Z |
|---|---|---|---|---|
| 1 | —CH= | H | —O— | —O— |
| 2 | —N= | NMe₂ | —O— | —O— |
| 3 | —N= | pyrrolidinyl | —O— | —O— |
| 4 | —N= | piperidinyl | —O— | —O— |
| 5 | —CH= | morpholinyl | —O— | —O— |
| 6 | —CH= | H | —O— | —S— |
| 7 | —N= | NMe₂ | —O— | —S— |
| 8 | —N= | pyrrolidinyl | —O— | —S— |
| 9 | —N= | piperidinyl | —O— | —S— |
| 10 | —CH= | morpholinyl | —O— | —S— |
| 11 | —CH= | H | —S— | —O— |
| 12 | —N= | NMe₂ | —S— | —O— |
| 13 | —N= | pyrrolidinyl | —S— | —O— |
| 14 | —N= | piperidinyl | —S— | —O— |
| 15 | —CH= | morpholinyl | —S— | —O— |
| 16 | —CH= | H | —S— | —S— |
| 17 | —N= | NMe₂ | —S— | —S— |

TABLE 5-continued (I-E-1)

| No. | E | R⁶ | A | Z |
|---|---|---|---|---|
| 18 | —N= | pyrrolidinyl | —S— | —S— |
| 19 | —N= | piperidinyl | —S— | —S— |
| 20 | —CH= | morpholinyl | —S— | —S— |

[Preparation of the Compound of the Present Invention]

(1) Among the compounds of the present invention represented by formula (I), a compound in which $R^1$ represents C1-8 alkyl, i.e., a compound represented by formula (IA)

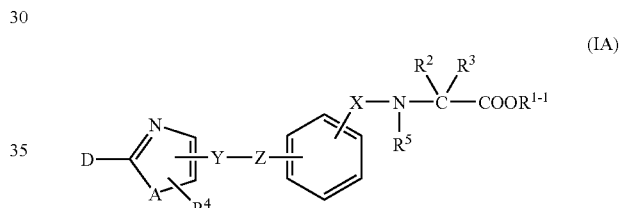

(IA)

(wherein $R^{1-1}$ represents C1-8 alkyl, and other symbols have the same meanings as described above.) can be prepared by reacting a compound represented by formula (II)

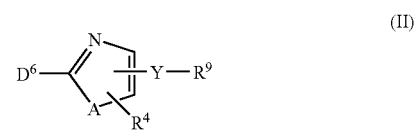

(II)

(wherein $R^9$ represents a leaving group (halogen atom, mesyloxy or tosyloxy, etc.), $D^6$ has the same meaning as D, with the proviso that amino in the group represented by $D^6$ may be protected, if necessary, and other symbols have the same meanings as described above.) with a compound represented by formula (III)

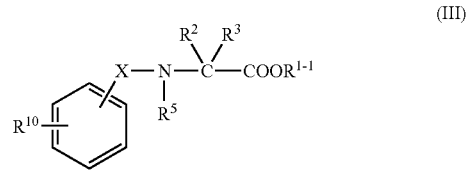

(III)

(wherein $R^{10}$ represents OH or SH and other symbols have the same meanings as described above.), if necessary, followed by subjecting to a deprotection reaction of the protective group.

This reaction is known. For example, it is carried out at 0 to 80° C. in an organic solvent (e.g., tetrahydrofuran (THF), diethyl ether, methylene chloride, chloroform, carbon tetrachloride, pentane, hexane, benzene, toluene, dimethylformamide (DMF), dimethylsulfoxide (DMSO), hexamethylphosphoramide (HMPA), etc.) in the presence of a base (sodium hydride, potassium carbonate, triethylamine, pyridine, sodium iodide, cesium carbonate, etc.).

The deprotection reaction of the protective group may be carried out by following method.

The deprotection reaction of the protective group of an amino is well known, and examples include:

(1) a deprotection reaction under acidic condition, or (2) a deprotection reaction by hydrogenolysis etc.

These methods are described below concretely.

(1) The deprotection reaction under acidic condition may be carried out, for example, in an organic solvent (methylene chloride, chloroform, dioxane, ethyl acetate, anisole, methanol, ethanol, isopropylalcohol etc.) or absence, or an aqueous solution thereof, using an organic acid (acetic acid, trifluoroacetic acid, methanesulfonic acid etc.) or an inorganic acid (hydrochloric acid, sulfuric acid etc.) or a mixture thereof (hydrogen bromide/acetic acid etc.), at 0 to 100° C.

(2) The deprotection reaction by hydrogenolysis may be carried out, for example, in a solvent (ether-type (tetrahydrofuran, dioxane, dimethoxyethane, diethyl ether etc.), alcohol-type (e.g., methanol, ethanol etc.), benzene-type (e.g., benzene, toluene etc.), ketone-type (e.g., acetone, methyl ethyl ketone etc.), nitrile-type (e.g., acetonitrile etc.), amide-type (e.g., dimethylformamide etc.), water, ethyl acetate, acetic acid, or mixed solvent of two or more of these etc.), in the presence of a catalyst (e.g., palladium-carbon, palladium-black, palladium hydroxide, platinum oxide, Raney nickel etc.), under ordinary or forced pressure in an atmosphere of hydrogen or in the presence ammonium formate, at 0 to 200° C.

The amino-protective group includes, for example, benzyloxycarbonyl, t-butoxycarbonyl, trifluoroacetyl, 9-fluorenylmethoxycarbonyl etc.

The amino-protective group is not particularly limited to the above, and other groups can be used. So long as they can he easily and selectively removed. For example, those described in T. W. Greene, *Protective Groups in Organic Synthesis,* 3rd Ed., Wiley, New York, 1999 may be used.

The intended compounds of the invention may be readily prepared through selective use of the deprotecting reaction, which could be readily understood by anyone skilled in the art.

(2) Among the compounds of the present invention represented by formula (I), a compound in which $R^1$ represents C1-8 alkyl and Z represents —O—, i.e., a compound represented by formula (IB)

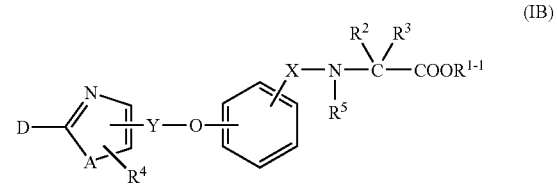

(wherein all symbols have the same meanings as described above.) can be prepared by reacting a compound represented by formula (IV)

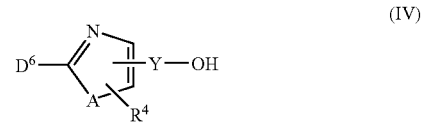

(wherein all symbols have the same meanings as described above.) with a compound represented by formula (III-1)

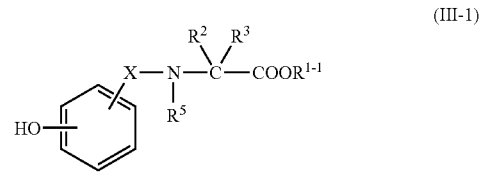

(wherein all symbols have the same meanings as described above.), if necessary, followed by subjecting to a deprotection reaction of the protective group.

This reaction is known. For example, it is carried out at 0 to 60° C. by reacting with a corresponding alcohol compound in an organic solvent (dichloromethane, diethyl ether, tetrahydrofuran, acetonitrile, benzene, toluene, etc.) in the presence of an azo compound (diethyl azodicarboxylate, diisopropyl azodicarboxylate, 1,1'-(azodicarbonyl)dipiperidine, 1,1'-azobis(N,N-dimethylformamide), etc.) and a phosphine compound (triphenylphosphine, tributylphosphine, trimethylphosphine, etc.).

The deprotection reaction of the protective group may be carried out by the methods described above.

(3) Among the compounds of the present invention represented by formula (I), a compound in which $R^1$ represents hydrogen, i.e., a compound represented by formula (IC)

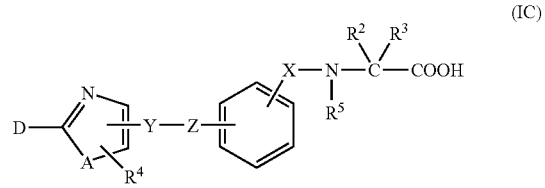

(wherein all symbols have the same meanings as described above.) can be prepared by subjecting the above compound represented by formula (IA) or (IB) to a hydrolysis reaction.

The said hydrolysis reaction is known. It is carried out, for example, (1) in an organic solvent admissible with water (THF, dioxane, ethanol, methanol etc.) or mixture solvent thereof, using an aqueous solution of alkali (potassium hydroxide, sodium hydroxide, lithium hydroxide, potassium carbonate, sodium carbonate etc.), or
(2) in alkanol (methanol, ethanol etc.), using the above alkali under an anhydrous condition. These reactions may be carried out at 0 to 100° C. normally.

The compounds represented by formulae (II) and (IV) are known compounds or can be prepared easily by known methods or methods described in Examples.

For example, among the compounds of formula (IV), 2-(5-methyl-2-phenyloxazol-4-yl)ethanol can be prepared by the methods described in *J. Med. Chem.*, 35, 1853-1864 (1992).

For example, among the compounds of formula (IV), 2-(5-methyl-2-(morpholin-4-yl)oxazol-4-yl)ethanol can be prepared by the methods described in *J. Med. Chem.*, 41, 5037-5054(1998).

For example, the compound represented by formula (III) can be prepared by the methods shown by the following Reaction Scheme 1.

In the reaction scheme 1, $R^{11}$ represents a protecting group of hydroxy, $X^1$ represents C1-3 alkylene, and other symbols have the same meanings as described above.

In Reaction Scheme 1, the compounds used as the starting materials represented by formulae (V) and (VII) are known compounds or can be prepared easily by known methods.

In each reaction described herein, the reaction product can be purified by general purification techniques such as distillation under ordinary pressure or a reduced pressure, high performance liquid chromatography, thin layer chromatography or column chromatography using silica gel or magnesium silicate, washing and recrystallization. Purification may be carried out in each reaction or after completion of several reactions.

[Pharmacological Activity]

It was confirmed that compounds of the present invention of formula (I) has PPAR regulating activities by the following experiments.

Measurement of PPAR α agonistic and PPAR γ agonistic activities:
(1) Preparation of materials in luciferase assay using human PPAR α or γ

The whole operations were carried out by the basic methods in gene engineering techniques and the conventional methods in yeast One-hybrid or Two-hybrid system.

As a luciferase gene expression vector under the control of thymidine kinase (TK) promotor, luciferase structural gene was excised from PicaGene Basic Vector 2 (trade

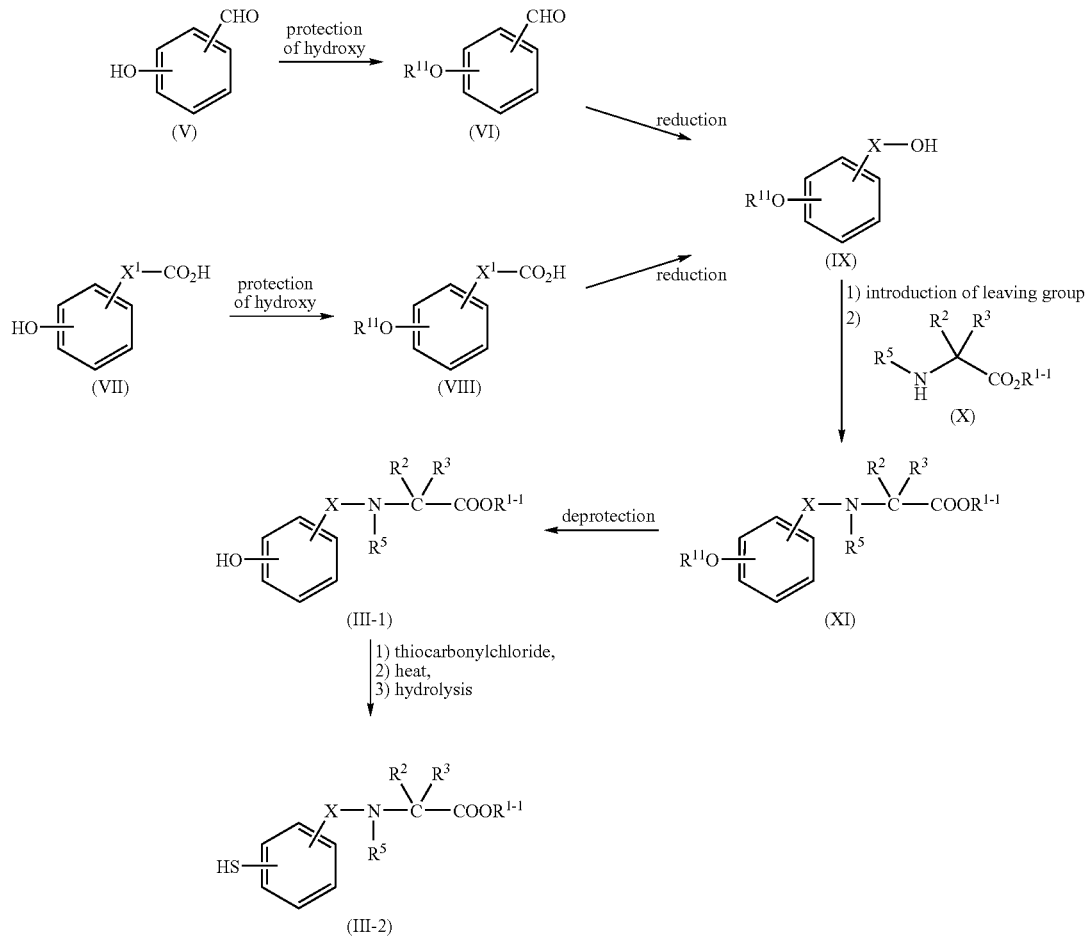

Reaction Scheme 1 name, Toyo Ink Inc., catalogue No. 309-04821), to prepare luciferase gene expression vector pTK-Luc. under the control of TK promotor (−105/+51) as a minimum essential promotor activity from pTKβ having TK promotor (Chrontech Inc., catalogue No. 6179-1). In the upper stream of TK promotor, four times repeated UAS sequence was inserted, which is the response element of Gal4 protein, a basic transcription factor in yeast, to construct 4×UAS-TK-Luc. as reporter gene. The following is the enhancer sequence used (SEQ ID NO:1).

SEQ ID NO:1: Enhancer Sequence Repeating Gal4 Response Element Four-times Tandemly.

5'-T(CGACGGAGTACTGTCCTCCG)×4 AGCT-3'

A vector was prepared as described hereafter which expresses chimeric receptor protein wherein in carboxy terminus of yeast Gal4 protein DNA binding domain was fused to ligand binding domain of human PPAR α or γ. That is to say, PicaGene Basic Vector 2 (trade name, Toyo Ink Inc., catalogue No. 309-04821) was used as a basic expression vector, the structural gene was exchanged for that of chimeric receptor protein, while promotor and enhancer domains were kept as they were.

DNA encoding a fused protein composed of Gal4 DNA binding domain, the 1st to 147th amino acid sequence linked to the ligand binding domain of human PPAR α or γ in frame was inserted to the downstream of promotor/enhancer in PicaGene Basic Vector 2 (trade name, Toyo Ink Inc., catalogue No. 309-04821). Here the DNA was aligned as follows; in the amino terminus of human PPAR α or γ ligand binding domain, nuclear translocation signal originated from SV-40 T-antigen, Ala Pro Lys Lys Lys Arg Lys Val Gly (SEQ ID NO:2) was added to make fusion protein localizing intranuclearly. On the other hand, in the carboxy terminus of them, influenza hemagglutinin epitope, Tyr Pro Tyr Asp Val Pro Asp Tyr Ala (SEQ ID NO:3) and stop codon for translation was added in this order, to detect an expressed fused protein tagged epitope sequence.

According to the comparison of human PPAR structures described in the literatures by R. Mukherjee et al. (see *J. Steroid Biochem. Molec. Biol*, 51, 157 (1994)), M. E. Green et al., (see *Gene Expression.*, 4, 281 (1995)), A. Elbrecht et al. (see *Biochem Biophys. Res. Commun.*, 224, 431 (1996)) or A. Schmidt et al. (see *Mol. Endocrinology*, 6, 1634 (1992)), the portion of structural gene used as ligand binding domain of human PPAR α or γ was DNA encoding the following peptide:

human PPAR α ligand binding domain: $Ser^{167}$-$Tyr^{468}$
human PPAR γ ligand binding domain: $Ser^{176}$-$Tyr^{478}$ (each human PPAR γ1 ligand binding domain and human PPAR γ2 ligand binding domain is $Ser^{204}$-$Tyr^{506}$ which is identical sequence each other). In order to measure basal level of transcription, an expression vector containing DNA binding domain of Gal4 protein lacking in PPAR ligand binding domain, which is exclusively encoding the 1st to 147th amino acid sequence in Gal4 protein was also prepared.

(2) Luciferase assay using human PPAR α or γ

CV-1 cells used as host cells were cultured by a conventional technique. That is to say, Dulbecco's modified Eagle medium (DMEM) supplemented 10% bovine fetal serum (GIBCO BRL Inc., catalogue No. 26140-061) and 50 U/ml of penicillin G and 50 μg/ml of streptomycin sulfate were used to culture CV-1 cells under the atmosphere of 5% carbon dioxide gas at 37° C.

$2 \times 10^6$ cells were seeded in a 10 cm dish, and once washed with the medium without serum, followed by addition of the medium (10 ml) thereto. Reporter gene (10 μg), Gal4-PPAR expression vector (0.5 μg) and 50 μl of LipofectAMINE (GIBRO BRL Inc., catalogue No. 18324-012) were well mixed and added to the culture to introduce these DNAs into the host cells. They were cultured at 37° C. for 5 to 6 hours, and thereto was added 10 ml of medium containing 20% of dialyzed bovine fetal serum (GIBRO BRL Inc., catalogue No. 26300-061), and then cultured at 37° C. overnight. The cells were dispersed by trypsin, and they were again seeded in 96-well plates in a density of 8000 cells/100 ml of DMEM-10% dialyzed serum/well. Several hours after the cultivation, when cells were attached to the plastic ware, then 100 μl of DMEM-10% dialyzed serum containing the compounds of the present invention, whose concentration is twice as high as the final concentration of them, was added thereto. The culture was settled at 37° C. for 42 hours and the cells were dissolved to measure luciferase activity according to manufacturers instruction.

As to PPAR α agonistic activity, the relative activity of the compounds of the present invention (10 μM) was shown in Table 6, under the condition that luciferase activity was defined as 1.0 in case of carbacyclin (10 μM) as a positive control compound, which could activate transcription of luciferase gene significantly to PPAR α (see *Eur. J. Biochem.*, 233, 242 (1996); *Genes & Development*, 10, 974 (1996)).

As to PPAR γ agonistic activity, the relative activity of the compounds of the present invention (10 μM) was shown in Table 7, under the condition that luciferase activity was defined as 1.0 in case of troglitazone (10 μM) as a positive control compound, which could activate transcription of luciferase gene significantly to PPAR γ (see *Cell*, 83, 863 (1995); *Endocrinology*, 137, 4189 (1996) and *J. Med. Chem.*, 39, 665 (1996)) and has been already launched as hypoglycemic agent.

Furthermore, assay of each compound was carried out three times to examine its reproducibility and to confirm the dose dependent activity.

TABLE 6

| Compound No. | Relative Activity to a positive control compound (carbacyclin = 1) |
|---|---|
| Example 2 | 0.9 |

TABLE 7

| Compound No. | Relative Activity to a positive control compound (troglitazone = 1) |
|---|---|
| Example 2 | 11.5 |

For example, Hypoglycemic and hypolipidemic effects of the compounds of the present invention can be measured by the following methods.

Hypoglycemic and Hypolipidemic Effects (1):

Male, 8-weeks old KKAy/Ta Jcl mice (five mice per group) are pre-breaded individually in single cages for approximately one week and provided pellet diet and tap water from bottle of feed water ad libitum. Mice are acclimatized to switch over to milled diet for three days. On the first day of the experiment (Day 0), the body weight of mice are measured. Blood samples are collected from coccygeal vein using a microcapillary to measure plasma glucose concentration. Based on plasma glucose concentration, mice are divided into some groups (five mice per group) using a stratified randomization method. The body weight of mice are measured on the morning of the next day, and from the next day for six days they are given compounds by food mixture containing 0.03% (w/w), 0.01% (w/w) or 0.003% (w/w) of the compound of the present invention or by milled diet only. On the morning of the fourth and the seventh day, body weights and food intakes of them are determined to calculate the mean administered dose. On the morning of the sixth day, blood samples were collected from coccygeal vein to measure glucose and triglyceride (TG) levels. On the seventh day after measuring body weight, blood samples are collected from abdominal vena cava under anesthetized condition by ether to determine plasma insulin, non-esterified fatty acid (NEFA), GOT and GPT levels using commercially available kits. And, the liver is removed and weighed. The total RNAs are prepared from left lobe of the liver and measured a gene expression level of bi-functional protein by Northern blot method. Actually, there is no significant difference in the food intake between control group (milled diet only) and compounds-treated group (milled diet containing 0.03%, 0.01% or 0.003% of compounds). The calculated dose is approximately 40 mg/kg/day in the group given diet containing 0.03% of the compound.

It is suggested the possibility as an agent for preventing and/or treating of diabetes mellitus, hyperlipidemia, atherosclerosis etc., from ameliorating effects of plasma glucose, plasma insulin, NEFA or TG levels in well-fed KKAy/Ta mice. This effect is likely to be mediated through PPAR γ activation in vivo. Additionally, it is likely that an increase in liver weight and in an expression of HD mRNA depends on PPAR α activation in vivo.

Hypoglycemic and Hypolipidemic effects (2):

Male, 8-weeks old Zucker fa/fa rats (Strain: Crj-[ZUC]-fa/fa) and healthy Zurker lean rats (Strain: Crj-[ZUC]-lean) to be contrasted are pre-breaded individually in single cages for approximately two weeks and provided pellet diet and tap water from automatic water supplying equipment ad libitum. For five days before the treatment, rats are acclimatized to oral gavage administration. During this period, a general condition of them is observed, and healthy rats with 10-weeks of age are used for experiment. The body weight of each rats are measured on the morning of the first day of experiment (Day 0) and blood samples are collected from coccygeal vein using a microcapillary to measure plasma glucose, TG, NEFA concentrations and HbA1c. Based on the HbA1c and body weight, rats are assigned to groups comprised of five animals each using a stratified randomization method. Additionally, rats are interchanged optionally to prevent the deflection of other parameters' averages between groups. The body weight of each animal was measured every morning from the day after grouping. Volumes to be administered are calculated on the basis of body weight measured on the day of administration, and oral gavage administration of compound of the present invention or vehicle only (0.5% methylcellulose) is conducted once a day for 13 days. The healthy animals (lean rats) are given vehicle only.

Food consumption is measured on the morning of Day 1, 4, 7, 10 and 13 to calculate mean food intakes. On the seventh day, blood samples are corrected from coccygeal vein using microcapillary to measure plasma glucose, TG, NEFA concentrations and HbA1c. And on the 14th day, oral glucose tolerance test (OGTT) is performed to evaluate improving effect on glucose intolerance. Rats are fasted on the previous day (Day 13) to perform OGTT. After blood samples are collected on the next day (Day 14), 40% glucose solution is loaded at a volume of 2 g/5 ml/kg per oral administration. 60 and 120 minutes after loading, blood samples are collected from coccygeal vein using microcapillary to determine plasma glucose levels.

Animals are given food after the OGTT and administered compound of the present invention on Day 15. On the morning of the 16th day after measuring body weight, blood samples are collected from abdominal vena cava under anesthetized condition by ether to determine plasma glucose, plasma insulin, TG, NEFA, GOT and GPT levels. And, the liver is removed and weighed.

It is suggested the possibility as an agent for preventing and/or treating of diabetes mellitus, hyperlipidemia, atherosclerosis etc., from ameliorating effects of plasma glucose, plasma insulin, TG, NEFA levels or HbA1c in well-fed Zucker fa/fa rats. Also, a decrease effect of fasting plasma glucose and improving effect of glucose intolerance during OGTT suggest the possibility as an agent for preventing and/or treating of diabetes mellitus. These effects are likely to be mediated through PPAR γ activation in vivo. Additionally, it is suggested that an increase in liver weight depends on PPAR α activation in vivo.

Hypoglycemic and Hypolipidemic Effects (3):

Male, 3- to 4-years old cynomolgus monkeys (Mean body weight: approximately 3 kg) to have a regal medical inspection are performed a medical inspection and acclimatized to be provided approximately 100 g of pellet diet once a day and tap water from automatic water supplying equipment ad libitum, individually in single monkey cages for more than one month. After then, animals become to take a diet within one hour. Additionally, animals are pre-breaded for 14 days. 14 and 7 days before the treatment, the body weight are measured, and then blood samples are collected from hindlimb saphenous vein to measure hematological (red blood cells-, hematocrit, hemoglobin, platelet and leukocytes) and biochemical (GOT, GPT, alkaline phosphatase, total protein, blood urea nitrogen, creatinine, creatinine kinase, total bilirubin, glucose, total cholesterol, HDL, LDL and TG) parameters. Additionally, a general condition of animals is observed during acclimatizing and pre-breeding, and healthy animals are used for experiment. Also, food consumption is measured everyday.

On the basis of body weight measured on the final day of acclimatizing period, animals are divided into some groups (three animals per group) using a stratified randomization method. On the morning of Day 1, 3, 7, 10 and 14, body weight is measured. Volumes to be administered are calculated based on the latest body weight, and oral gavage administration with compound of the present invention (3-100 mg/kg/day) or vehicle alone (diluted solution) is conducted once a day for 14 days. 1, 7 and 14 days after the treatment, blood samples are collected to measure the above mentioned hematological and biochemical parameters before the administration of the compound of the present invention. It confirms that blood glucose is not changed with the compound of the present invention. Three weeks before, and 14 days after the start of treatment, blood samples are collected from hindlimb saphenous vein or antebrachial vein at 1, 2 and 4 hours after oral gavage, and also at 1, 2 and 3 hours after providing a diet, to measure plasma glucose and TG.

It is suggested the possibility as an agent for preventing and/or treating of hyperlipidemia and atherosclerosis etc., from ameliorating effects of plasma TG levels in fasted monkeys. These effects are likely to be mediated through PPAR α activation in vivo. It is also observed in suppressing effect on post-prandial TG increase. Additionally, it can be estimated whether compound have a toxicity risk from other biochemical parameters.

[Toxicity]

The toxicity of the compound represented by formula (I) of the present invention is very low so that it is considered that the compound is sufficiently safe for using as a pharmaceutical.

INDUSTRIAL APPLICABILITY

[Application to Pharmaceutical]

Since the compound represented by formula (I) of the present invention and nontoxic salt thereof have a PPAR modulating activity, it is expected to be applied as hypoglycemic agents, hypolipidemic agents, agents for preventing and/or treating of diseases associated with metabolic disorders such as diabetes, obesity, syndrome X, hypercholesterolemia and hyperlipoproteinemia etc., hyperlipidemia, atherosclerosis, hypertension, circulatory diseases, overeating, ischemic heart diseases etc., HDL cholesterol-elevating agents, LDL cholesterol and/or VLDL cholesterol-lowering agents and agents for relieving risk factors of diabetes or syndrome X.

Also, since the compound represented by formula (I) of the present invention, and non-toxic salts thereof, have a PPARα agonist and/or PPAR γ agonist effect, it is expected to be applied as hypoglycemic agents, hypolipidemic agents, agents for preventing and/or treating of diseases associated with metabolic disorders such as diabetes, obesity, syndrome X, hypercholesterolemia, hyperlipoproteinemia etc., hyperlipidemia, atherosclerosis, hypertension, circulatory diseases and overeating etc., HDL cholesterol-elevating effect, LDL cholesterol and/or VLDL cholesterol-lowering effect, inhibition of progress of atherosclerosis and its treatment, and inhibitory effect against obesity. They are also expected to be useful for the treatment and/or prevention of diabetes as hypoglycemic agents, for the amelioration of hypertension, for the relief from risk factors of syndrome X, and as agents for preventing against occurrence of ischemic heart diseases.

In the present invention, the compound represented by formula (I) may be administered in combination with other drugs for the purpose of 1) complement and/or enhancement of preventing and/or treating effect, 2) improvement of dynamics and absorption of the compound, and lowering of dose, and/or 3) alleviation of side effect of the compound.

The compound represented by formula (I) may be administered in combination with other drugs as a composition in one drug product comprising these components, or may be administered separately. When they are administered independently, they may be administered simultaneously or with time lag. Administering with time lag includes the method of administering the compound represented by formula (I) before other drugs and vice versa; they may be administered in the same route or not.

The above combination takes effects on whichever disease treating and/or preventing effect of the compound represented by formula (I) is complemented and/or enhanced.

As other drugs to complement and/or to enhance effect of the compound represented by formula (I), or to enhance effect of the treatment of complication of diabetes, for example, sulfonylurea type hypoglycemic agent, biguanide preparation, alfa-glucosidase inhibitor, fast-acting insulin secretion accelerator, insulin preparation, PPAR agonist, insulin sensitizer without PPAR agonistic activity, beta-3 adrenaline receptor activator, aldose reductase inhibitor or dipeptidyl peptidase IV inhibitor etc. are given.

Examples of sulfonylurea agents include acetohexamide, glibenclamide, gliclazide, glyclopyramide, chlorpropamide, tolazamide, tolbutamide and glimepiride, etc.

Examples of biguanide preparations include buformin hydrochloride and metformin hydrochloride, etc.

Examples of alfa-glucosidase inhibitors include acarbose and voglibose, etc.

Examples of fast-acting insulin secretion accelerators include nateglinide and repaglinide, etc.

Examples of PPAR agonists include pioglitazone, troglitazone, rosiglitazone and JTT-501, etc.

Examples of insulin sensitizers having no PPAR agonistic activity include, ONO-5816 and YM-440, etc.

Examples of beta-3 adrenaline receptor activators include AJ9677, L750355 and CP331648, etc.

Examples of aldose reductase inhibitors include epalrestat, fidarestat and zenarestat, etc.

The weight proportion of the compound represented by formula (I) and the other drugs is not specifically limited.

Arbitrary two or more of the other drugs may be administered in combination.

Examples of the other drugs for compensating for and/or enhancing the preventive and/or treatment effect of the compound represented by formula (I) include not only those which have so far been found but also those which will be found on the basis of the aforementioned mechanism.

When the compound represented by formula (I) of the present invention, or concomitant drug combined the compound represented by formula (I) with other drugs are used for the above-described purpose, it is usually administered systemically or topically via an oral or parenteral route.

The doses to be administered are determined depending upon, for example, age, body weight, symptom, the desired therapeutic effect, the route of administration, and the duration of the treatment. In the human adult, the doses per person are generally from 1 ng to 100 mg, by oral administration, up to several times per day, and from 0.1 ng to 10 mg, by parenteral administration, up to several times per day, or continuous administration from 1 to 24 hours per day from vein.

As mentioned above, the doses to be used depend upon various conditions. Therefore, there are cases in which doses lower than or greater than the ranges specified above may be used.

When the compound represented by formula (I) of the present invention, or concomitant drug combined the compound represented by formula (I) with other drugs are used for the above-described purpose, it is usually administered systemically or topically via an oral or parenteral route. It is desirable to choose the most effective administration route on the occasion of medical treatment.

The doses to be administered are determined depending upon, for example, age, body weight, symptom, the desired therapeutic effect, the route of administration, and the duration of the treatment. In the human adult, the doses per person are generally from 1 ng to 100 mg, by oral administration, up to several times per day, and from 0.1 ng to 10 mg, by parenteral administration, up to several times per day or continuous administration from 1 to 24 hours per day from vein.

As mentioned above, the doses to be used depend upon various conditions. Therefore, there are cases in which doses lower than or greater than the ranges specified above may be used.

The compound represented by formula (I) of the present invention, or concomitant drug combined the compound represented by formula (I) with other drugs may be administered in the composition of, for example, solid preparations for internal use and liquid preparations for internal use, each for oral administration, or injections, preparations for external use or suppositories, each for parenteral administration.

Examples of the solid preparations for internal use for oral administration include tablets, pills, capsules, powders, granules and the like. The capsules include hard capsules and soft capsules.

Such a solid preparation for internal use is prepared by a formulation method commonly employed by using one or more active substances either as such or as a mixture with an excipient (lactose, mannitol, glucose, microcrystalline cellulose, starch, etc.), a binder (hydroxypropylcellulose, polyvinylpyrrolidone, magnesium metasilicate aluminate, etc.), a disintegrating agent (calcium cellulose glycolate, etc.), a lubricant (magnesium stearate, etc.), a stabilizer, and a dissolution aid (glutamic acid, aspartic acid, etc.). If necessary, it may be coated with a coating agent (sucrose, gelatin, hydroxypropylcellulose, hydroxypropylmethylcellulose phthalate, etc.). It may be coated with two or more layers. Moreover, capsules made of an absorbable material such as gelatin are involved in the scope thereof.

The liquid preparations for internal use for oral administration involve pharmaceutically acceptable solutions, suspensions, emulsions, syrups, elixirs and the like. Such a liquid preparation is prepared by dissolving, suspending or emulsifying one or more active substances in a diluent commonly employed (purified water, ethanol, a mixture thereof, etc.). Besides such liquid forms may also comprise some additives, such as humectants, suspending agents, emulsifying agents, sweetening agents, flavoring agents, aroma, preservative or buffering agents etc.

The injections for parenteral administration involve solutions, suspensions, emulsions and solid injections to be dissolved or suspended before use. Such an injection is used by dissolving, suspending or emulsifying one or more active substances in a solvent. As a solvent, use may be made of, for example, distilled water for injection, physiological saline, vegetable oils, alcohols such as propylene glycol, polyethylene glycol or ethanol and mixtures thereof. The injection may further contain a stabilizer, a dissolution aid (glutamic acid, aspartic acid, Polysorbate 80 (registered trade name), etc.), a suspending agent, an emulsifier, a soothing agent, a buffer, a preservative, etc. Such an injection may be produced by sterilizing at the final step or employing aseptic process. Alternatively, it is also possible that an aseptic solid product such as a freeze-dried product is produced and sterilized or dissolved in aseptic distilled water for injection or another solvent before use.

The dosage forms of the parenteral administration preparations for external use involve ointments, gels, creams, fomentations, patches, liniments, atomized agents, inhalations, sprays, eye drops, nasal drops and the like. Such a preparation contains one or more active substances and is prepared by a publicly known method or in accordance with a formulation commonly employed.

Ointments are prepared in accordance with a publicly known formulation or a formulation commonly employed. For example, they are prepared by levigating or melting one or more active substances in a base. The ointment base is selected from among publicly known ones or those commonly employed. For example, use may be made of one base or a mixture of two or more thereof selected from higher fatty acids or higher fatty acid esters (adipic acid, myristic acid, palmitic acid, stearic acid, oleic acid, adipic acid esters, myristic acid esters, palmitic acid esters, stearic acid esters, oleic acid esters, etc.), waxes (beeswax, whale wax, ceresin, etc.), surfactants (polyoxyethylene alkyl ether phosphoric acid esters, etc.), higher alcohols (cetanol, stearyl alcohol, cetostearyl alcohol, etc.), silicone oils (dimethylpolysiloxane, etc.), hydrocarbons (hydrophilic vaseline, white vaseline, refined lanolin, liquid paraffin, etc.), glycols (ethylene glycol, diethylene glycol, propylene glycol, polyethylene glycol, macrogol, etc.), vegetable oils (castor oil, olive oil, sesame oil, turpentine oil, etc.), animal oils (mink oil, yolk oil, squalane, squalene, etc.), water, absorption promoters and skin irritation inhibitors. The ointments may further contain a humectant, a preservative, a stabilizer, an antioxidant, a flavor, etc.

Gels are prepared in accordance with a publicly known formulation or a formulation commonly employed. For example, they are prepared by melting one or more active substances in a base. The gel base is selected from among publicly known ones or those commonly employed. For example, use may be made of one base or a mixture of two or more thereof selected from among lower alcohols (ethanol, isopropyl alcohol, etc.), gelling agents (carboxymethylcellulose, hydroxyethylcellulose, hydroxypropylcellulose, ethylcellulose, etc.), neutralizing agents (triethanolamine, diisopropanolamine, etc.), surfactants (polyethylene glycol monostearate, etc.), gums, water, absorption promoters and skin irritation inhibitors. The gels may further contain a preservative, an antioxidant, a flavor, etc.

Creams are prepared in accordance with a publicly known formulation or a formulation commonly employed. For example, they are prepared by melting or emulsifying one or more active substances in a base. The cream base is selected from among publicly known ones or those commonly employed. For example, use may be made of one base or a mixture of two or more thereof selected from among higher fatty acid esters, lower alcohols, hydrocarbons, polyhydric alcohols (propylene glycol, 1,3-butylene glycol, etc.), higher alcohols (2-hexyldecanol, cetanol, etc.), emulsifiers (polyoxyethylene alkyl ethers, fatty acid esters, etc.), water, absorption promoters and skin irritation inhibitors. The creams may further contain a preservative, an antioxidant, a flavor, etc.

Fomentations are prepared in accordance with a publicly known formulation or a formulation commonly employed. For example, they are prepared by melting one or more active substances in a base, kneading and then applying and spreading the kneaded matter on a substrate. The fomentation base is selected from among publicly known ones or those commonly employed. For example, use may be made of one base or a mixture of two or more thereof selected from among thickeners (polyacrylic acid, polyvinylpyrrolidone, gum acacia, starch, gelatin, methylcellulose, etc.), moistening agents (urea, glycerin, propylene glycol, etc.), fillers (kaolin, zinc oxide, talc, calcium, magnesium, etc.), water, dissolution aids, tackifiers and skin irritation inhibitors. The fomentations may further contain a preservative, an antioxidant, a flavor, etc.

Patches are prepared in accordance with a publicly known formulation or a formulation commonly employed. For example, they are prepared by melting one or more active substances in a base and then applying and spreading on a substrate. The patch base is selected from among publicly known ones or those commonly employed. For example, use may be made of one base or a mixture of two or more thereof selected from among polymer bases, fats and oils, higher fatty acids, tackifiers and skin irritation inhibitors. The patches may further contain a preservative, an antioxidant, a flavor, etc.

Liniments are prepared in accordance with a publicly known formulation or a formulation commonly employed. For example, they are prepared by dissolving, suspending or emulsifying one or more active substances in one or more media selected from among water, alcohols (ethanol, polyethylene glycol, etc.), higher fatty acids, glycerin, soap, emulsifiers, suspending agents and the like. The liniments may further contain a preservative, an antioxidant, a flavor, etc.

Atomized agents, inhalations and sprays may contain, in addition to a diluent commonly employed, a stabilizer such as sodium hydrogen sulfite, a buffer for imparting isotonicity, for example, an isotonic agent such as sodium chloride, sodium citrate or citric acid. Methods for producing a spray are described in detail in, for example, U.S. Pat. Nos. 2,868,691 and 3,095,355. Moreover, it is used aerosol agents.

In case of administration of nasal drops, they may be usually sprayed intranasally in the form of liquid or powder comprising drugs with a special apparatus for nasal drops or nebulizer quantitatively.

Eye drops for parenteral administration may be in the form of liquid, suspension, emulsion, liquid dissolved in a solvent in use or ointment.

These eye drops are prepared by any known method. For example, one or more active substances are dissolved, suspended or emulsified in a solvent. As such a solvent for eye drops there may be used sterilized purified water, physiological saline and other aqueous or nonaqueous solvents (e.g., vegetable oil), singly or in combination thereof. The eye drops may contain one or more solvent optionally selected from an isotonic agent (e.g., sodium chloride, concentrated glycerin), a buffering agent (e.g., sodium phosphate, sodium acetate), a surfactants (e.g., Polysolvate 80 (trade name), polyoxyl stearate 40, polyoxyethylene-hardened castor oil), a stabilizer (sodium citrate, sodium edetate), a preservative (e.g., benzalconium chloride, paraben), etc. The eye drops are sterilized at the final step or prepared by an aseptic process. Alternatively, an aseptic solid agent such as freeze-dried product which has previously been prepared may be rendered aseptic or dissolved in an aseptic distilled water for injection or other solvent before use.

The inhalations for parenteral administration involve aerosols, powders for inhalation and liquids for inhalation. Such inhalations may be in the form to be dissolved or suspended in water or another adequate medium before use.

The inhalations may he prepared in accordance with a publicly known method.

For example, liquid preparations for inhalation may be prepared, if necessary, by appropriately selecting a preservative (benzalkonium chloride, paraben, etc.), a colorant, a buffer (sodium phosphate, sodium acetate, etc.), an isotonic agent (sodium chloride, concentrated glycerin, etc.), a thickener (carboxyvinyl polymer, etc.), an absorption promoter and the like.

Powders for inhalation may be prepared, if necessary, by appropriately selecting a lubricant (stearic acid, its salt, etc.), a binder (starch, dextrin, etc.), an excipient (lactose, cellulose, etc.), a colorant, a preservative (benzalkonium chloride, paraben, etc.), an absorption promoter, etc.

When the liquids for inhalation are administered, a sprayer (atomizer, nebulizer) is usually used. When the powders for inhalation are used, an inhalation administration apparatus for powder agents is usually used.

Other compositions for parenteral administration include suppositories and pessaries for vaginal administration which contain one or more active substances and are prepared in accordance with common formulations.

BEST MODE FOR CARRYING OUT THE INVENTION

The present invention is explained below in detail based on Reference Examples and Examples, however, the present invention is not limited thereto.

The solvents in the parentheses show the developing or eluting solvents and the ratios of the solvents used are by volume in chromatographic separations or TLC. The solvents in the parentheses in NMR show the solvents for measurement. MOMO represents methoxymethoxy group.

REFERENCE EXAMPLE 1

3-methoxymethoxybenzaldehyde

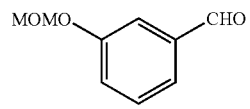

To a solution of 3-hydroxybenzaldehyde (1.0 g) in tetrahydrofuran (25 mL) was added sodium hydride (374 mg) at 0° C. and the mixture was stirred at 0° C. for 20 minutes. Methoxymethylchloride (0.92 mL) was added to the reaction mixture, which was stirred for 30 minutes at room temperature. The reaction mixture was poured into cold water and extracted with ethyl acetate. The organic layer was washed with brine, dried over anhydrous magnesium sulfate and concentrated. The residue was purified by column chromatography on silica gel (hexane:ethyl acetate=8:1→5:1) to give the title compound (1.36 g) having the following physical data.

TLC: Rf 0.69 (hexane:ethyl acetate=2:1);

NMR (CDCl$_3$): δ 9.98 (s, 1H), 7.62-7.40 (m, 3H), 7.30 (m, 1H), 5.24 (s, 2H), 3.50 (s, 3H).

REFERENCE EXAMPLE 2

3-methoxymethoxybenzylalcohol

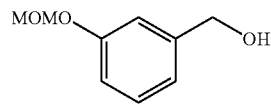

Into a suspension of lithium aluminum hydride (178 mg) in tetrahydrofuran (15 mL) was dropped a solution of the compound prepared in Reference Example 1 (1.30 g) in tetrahydrofuran (24 mL) at 0° C. and the mixture was stirred at 0° C. for 20 minutes. A saturated aqueous sodium sulfate solution was dropped into the reaction mixture and then ether was added thereto. The reaction mixture was dried over anhydrous magnesium sulfate and concentrated to give the crude title compound (1.39 g) having the following physical data. The obtained compound was used in the next reaction without purification.

TLC: Rf 0.25 (hexane:ethyl acetate=2:1);

NMR (CDCl$_3$): δ 7.28 (dd, J=7.8, 7.8 Hz, 1H), 7.10-6.92 (m, 3H), 5.19 (s, 2H), 4.67 (brd, J=3.0 Hz, 2H), 3.48 (s, 3H).

REFERENCE EXAMPLE 3

2-(N-allyl-N-(3-methoxymethoxybenzyl)amino)acetic acid ethyl ester

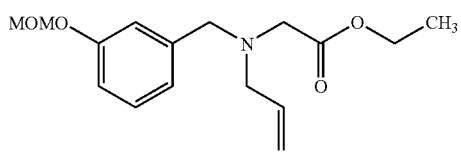

To a solution of the compound prepared in Reference Example 2 in tetrahydrofuran (16 mL) were added triethylamine (2.0 mL) and tosyl chloride (0.72 mL) at 0° C. and the mixture was stirred for 40 minutes at 0° C. Ethanol (0.23 mL) was added to the reaction mixture, which was stirred for 20 minutes at 0° C. A solution of acetonitrile (5.0 mL), potassium carbonate (2.16 g) and N-allylglycine ethyl ester (1.68 g) in acetonitrile (18 mL) was added to the reaction mixture, which was stirred for 40 minutes at 75° C. The reaction mixture was cooled to room temperature, then poured into cold water and extracted with ethyl acetate. The organic layer was washed with brine, dried over anhydrous magnesium sulfate and concentrated. The residue was purified by column chromatography on silica gel (hexane:ethyl acetate=8:1→6:1) to give the title compound (1.84 g) having the following physical data.

TLC: Rf 0.40 (hexane:ethyl acetate=5:1);

NMR (CDCl$_3$): δ 7.23 (dd, J=7.8, 7.8 Hz, 1H), 7.08-6.90 (m, 3H), 5.88 (ddt, J=16.8, 10.2, 6.6 Hz, 1H), 5.28-5.10 (m, 2H), 5.17 (s, 2H), 4.16 (q, J=7.2 Hz, 2H), 3.77 (s, 2H), 3.48 (s, 3H), 3.32 (s, 2H), 3.28 (d, J=6.6 Hz, 2H), 1.27 (t, J=7.2 Hz, 3H).

REFERENCE EXAMPLE 4

2-(N-allyl-N-(3-hydroxybenzyl)amino)acetic acid ethyl ester

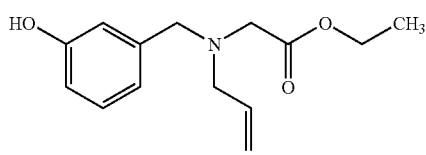

To a solution of the compound prepared in Reference Example 3 (1.80 g) in ethanol (6.1 mL) was added 4N hydrogen chloride-dioxane solution (3.1 mL) and the mixture was stirred overnight at room temperature. The reaction mixture was poured into a cold saturated aqueous sodium hydrogen carbonate solution and extracted with ethyl acetate. The organic layer was washed with brine, dried over anhydrous magnesium sulfate and concentrated to give the title compound (1.61 g) having the following physical data.

TLC: Rf 0.39 (hexane:ethyl acetate=2:1);

NMR (CDCl$_3$): δ 7.17 (dd, J=7.8, 7.8 Hz, 1H), 6.94-6.84 (m, 2H), 6.73 (m, 1H), 5.87 (ddt, J=16.8, 10.2, 6.6 Hz, 1H), 5.28-5.10 (m, 2H), 4.15 (q, J=6.9 Hz, 2H), 3.73 (s, 2H), 3.31 (s, 2H), 3.26 (d, J=6.6 Hz, 2H), 1.26 (t, J=6.9 Hz, 3H).

REFERENCE EXAMPLE 5

6-(perhydroazepin-1-yl)nicotinic acid

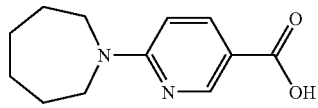

A suspension of 6-chloronicotinic acid (5.0 g) and perhydroazepine (7.16 mL) in xylene (20 mL) was stirred at 140° C. for 30 hours under an atmosphere of argon. The reaction mixture was cooled to room temperature, diluted with hexane and filtrated. The insoluble material was dissolved in ethyl acetate. The organic layer was washed with water and brine sequentially, dried over anhydrous magnesium sulfate and concentrated to give the title compound (3.19 g) having the following physical data.

TLC: Rf 0.21 (chloroform:methanol=9:1).

REFERENCE EXAMPLE 6

3-methoxycarbonyl-2-(6-(perhydroazepin-1-yl)pyridin-3-ylcarbonylamino)propionic acid benzyl ester

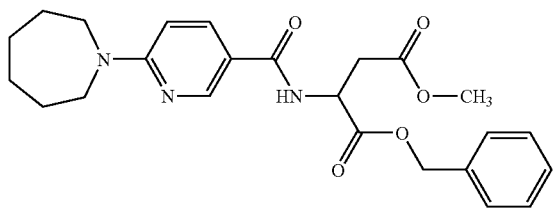

To a solution of the compound prepared Reference Example 5 (3.19 g) and 3-amino-3-benzyloxycarbonylpropionic acid methyl ester hydrochloride (4.38 g) in anhydrous dimethylformamide (40 mL) were added 1-ethyl-3-(3-dimethylaminopropyl)carbodiimide (3.34 g) and triethylamine (4.45 mL), and the mixture was stirred at room temperature for 15 hours. The reaction mixture was diluted with water and extracted with ethyl acetate. The organic layer was washed with water and brine sequentially, dried over anhydrous magnesium sulfate and concentrated. The residue was purified by column chromatography on silica gel (hexane: ethyl acetate=3:1) to give the title compound (2.94 g) having the following physical data.

TLC: Rf 0.77 (chloroform:methanol=9:1).

REFERENCE EXAMPLE 7

3-methoxycarbonyl-2-(6-(perhydroazepin-1-yl)pyridin-3-ylcarbonylamino)propionic acid

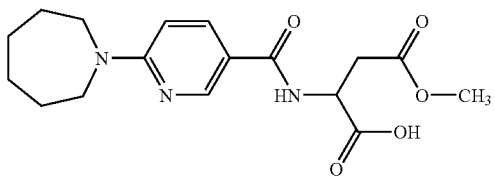

To a suspension of 10% palladium-carbon (300 mg, 50% wet) in ethanol (10 mL) was added a solution of the compound prepared in Reference Example 6 (2.94 g) in ethanol (15 mL) and the mixture was stirred at room temperature for 2 hours under an atmosphere of hydrogen. The reaction mixture was filtrated and concentrated to give the title compound having the following physical data.

TLC: Rf 0.10 (chloroform:methanol=9:1).

REFERENCE EXAMPLE 8

3-acetyl-3-(6-(perhydroazepin-1-yl)pyridin-3-ylcarbonylamino)propionic acid methyl ester

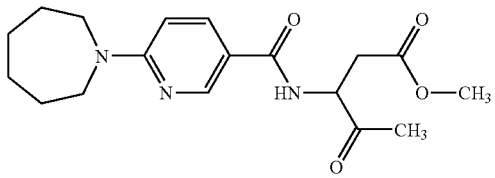

To a solution of the compound prepared in Reference Example 7 and 4-dimethylaminopyridine (40 mg) in anhydrous pyridine (10 mL) was added acetic anhydride (1.26 mL) and the mixture was stirred at 80° C. for 15 hours. The reaction mixture was cooled to room temperature and concentrated to give the title compound having the following physical data.

TLC: Rf 0.20 (hexane:ethyl acetate=1:1).

REFERENCE EXAMPLE 9

2-(2-(6-(perhydroazepin-1-yl)pyridin-3-yl)-5-methyloxazol-4-yl)acetic acid methyl ester

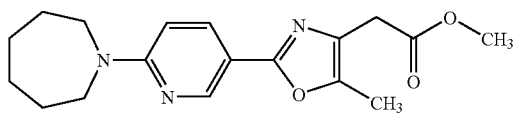

To a solution of the compound prepared in Reference Example 8 in acetic anhydride (20 mL) was added concentrated sulfuric acid (2 mL) and the mixture was stirred at 90° C. for 2 hours. The reaction mixture was cooled to room temperature, neutralized with a saturated aqueous potassium carbonate solution and extracted with ethyl acetate. The organic layer was washed with water and brine sequentially, dried over anhydrous magnesium sulfate and concentrated. The residue was purified by column chromatography on silica gel (hexane:ethyl acetate=2:1) to give the title compound (1.44 g) having the following physical data.

TLC: Rf 0.44 (hexane:ethyl acetate=1:1);

NMR (CDCl$_3$): δ 8.71 (d, J=2.4 Hz, 1H), 7.96 (dd, J=9.0, 2.4 Hz, 1H), 6.50 (d, J=9.0 Hz, 1H), 3.72 (s, 3H), 3.67 (dd, J=6.0:5.7 Hz, 4H), 3.54 (s, 2H), 2.33 (s, 3H), 1.83-1.77 (m, 4H), 1.60-1.52 (m, 4H).

REFERENCE EXAMPLE 10

2-(2-(6-(perhydroazepin-1-yl)pyridin-3-yl)-5-methyloxazol-4-yl)ethanol

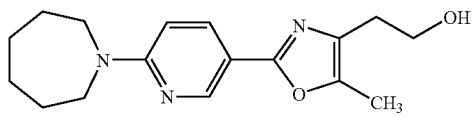

Under an atmosphere of argon, into a suspension of lithium aluminum hydride (166 mg) in anhydrous tetrahydrofuran (10 mL) was dropped a solution of the compound prepared in Reference Example 9 (1.44 g) in anhydrous tetrahydrofuran (10 mL) at 0° C. and the mixture was stirred at room temperature for 2 hours. The reaction mixture was cooled to 0° C. Methanol (1.0 mL) was dropped into the reaction mixture, which was stirred for 15 minutes. The reaction mixture was diluted with diisopropyl ether. A saturated aqueous sodium carbonate solution (10 mL) was added to the dilution, which was stirred at room temperature for 1 hour. The reaction mixture was filtrered through the filter layered over sodium sulfate. The insoluble material was washed with diisopropyl ether. The combined organic layer was concentrated to give the title compound (1.20 g) having the following physical data.

TLC: Rf 0.45 (ethyl acetate);

NMR (CDCl$_3$): δ 8.72 (d, J=2.4 Hz, 1H), 7.94 (dd, J=9.0, 2.4 Hz, 1H), 6.51 (d, J=9.0 Hz, 1H), 3.94-3.87 (m, 2H), 3.68 (dd, J=6.3, 5.7 Hz, 4H), 3.47-3.40 (m, 1H), 2.69 (t, J=6.0 Hz, 2H), 2.30 (s, 3H), 1.83-1.77 (m, 4H), 1.62-1.52 (m, 4H).

EXAMPLE 1

2-(N-allyl-N-(3-(2-(2-(6-(perhydroazepin-1-yl)pyridin-3-yl)-5-methyloxazol-4-yl)ethoxy)benzyl)amino)acetic acid ethyl ester

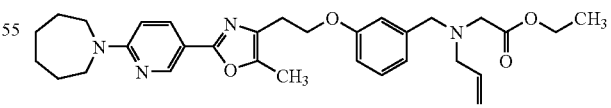

Under an atmosphere of argon, to a solution of the compound prepared in Reference Example 10 (500 mg) and the compound prepared in Reference Example 4 (623 mg) in anhydrous methylene chloride (30 mL) were added triphenylphosphine (656 mg) and 1,1'-(azodicarbonyl)dipyperidine (631 mg) at room temperature and the mixture was stirred for 18 hours. The reaction mixture was concentrated and the residue was diluted with diethylether and filtrated.

The filtrate was washed with 2N aqueous sodium hydroxide solution, water and brine sequentially, dried over anhydrous magnesium sulfate and concentrated. The residue was purified by column chromatography on silica gel (hexane:ethyl acetate=4:1) to give the compound of the present invention (777 mg) having the following physical data.

TLC: Rf 0.47 (hexane:ethyl acetate=1:1);

NMR (CDCl$_3$): δ 8.71 (d, J=2.4 Hz, 1H), 7.96 (dd, J=9.0, 2.4 Hz, 1H), 7.20 (dd, J=7.8, 7.5 Hz, 1H), 6.92-6.88 (m, 2H), 6.82-6.77 (m, 1H), 6.50 (d, J=9.0 Hz, 1H), 5.94-5.80 (m, 1H), 5.23-5.12 (m, 2H), 4.22 (t, J=6.9 Hz, 2H), 4.14 (q, J=6.9 Hz, 2H), 3.76 (s, 2H), 3.68 (dd, J=6.3, 5.7 Hz, 4H), 3.30 (s, 2H), 3.27 (d, J=6.6 Hz, 2H), 2.95 (t, J=6.9 Hz, 2H), 2.34 (s, 3H), 1.83-1.77 (m, 4H), 1.58-1.52 (m, 4H), 1.24 (t, J=6.9 Hz, 3H).

EXAMPLE 1(1)-EXAMPLE 1(17)

By the same procedure as described in Example 1 using the corresponding alcohol derivatives instead of the compound prepared in Reference Example 11, and the compound prepared in Reference Example 5 or the corresponding phenol derivatives, the following compounds of the present invention were obtained.

EXAMPLE 1(1)

2-(N-allyl-N-(3-(2-(2-isopropyl-5-methyloxazol-4-yl)ethoxy)benzyl)amino)acetic acid ethyl ester

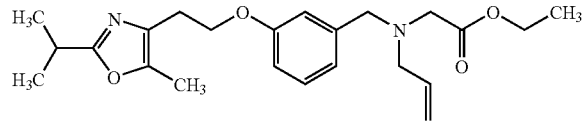

TLC: Rf 0.35 (hexane:ethyl acetate=4:1).

EXAMPLE 1(2)

2-(N-allyl-N-(3-(2-(2-(4-methylpiperazin-1-yl)-5-methylthiazol-4-yl)ethoxy)benzyl)amino)acetic acid ethyl ester

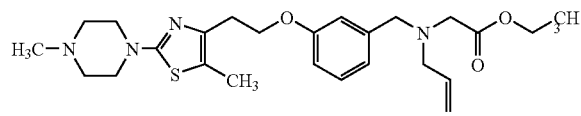

TLC: Rf 0.43 (chloroform:methanol=10:1);

NMR (CDCl$_3$): δ 7.19 (dd, J=8.0, 8.0 Hz, 1H), 6.93-6.86 (m, 2H), 6.78 (m, 1H), 5.87 (ddt, J=16.5, 10.0, 6.4 Hz, 1H), 5.21 (m, 1H), 5.15 (m, 1H), 4.19 (t, J=7.0 Hz, 2H), 4.15 (q, J=7.0 Hz, 2H), 3.75 (s, 2H), 3.46-3.37 (m, 4H), 3.30 (s, 2H), 3.27 (d, J=6.5 Hz, 2H), 2.95 (t, J=7.0 Hz, 2H), 2.56-2.48 (m, 4H), 2.33 (s, 3H), 2.25 (s, 3H), 1.26 (t, J=7.0 Hz, 3H).

EXAMPLE 1(3)

2-(N-allyl-N-(3-(2-(2-(4-(1,2,3-thiadiazol-4-yl)phenyl)-5-methyloxazol-4-yl)ethoxy)benzyl)amino)acetic acid ethyl ester

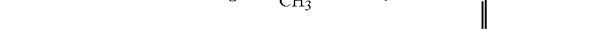

TLC: Rf 0.66 (hexane:ethyl acetate=1:1);

NMR (CDCl$_3$): δ 8.71 (s, 1H), 8.13 (s, 4H), 7.21 (dd, J=7.9, 7.9 Hz, 1H), 6.98-6.75 (m, 3H), 5.87 (m, 1H), 5.30-5.08 (m, 2H), 4.26 (t, J=6.6 Hz, 2H), 4.14 (q, J=7.2 Hz, 2H), 3.75 (s, 2H), 3.38-3.20 (m, 4H), 3.00 (t, J=6.6 Hz, 2H), 2.41 (s, 3H), 1.25. (t, J=7.2 Hz, 3H).

EXAMPLE 1(4)

2-(N-allyl-N-(3-(2-(2-(4-cyclohexylphenyl)-5-methyloxazol-4-yl)ethoxy)benzyl)amino)acetic acid ethyl ester

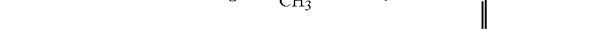

TLC: Rf 0.65 (hexane:ethyl acetate=2:1);

NMR (CDCl$_3$): δ 7.94-7.84 (m, 2H), 7.32-7.23 (m, 2H), 7.19 (dd, J=7.8, 7.8 Hz, 1H), 6.96-6.86 (m, 2H), 6.79 (m, 1H), 5.87 (ddt, J=17.1, 10.2, 6.6 Hz, 1H), 5.28-5.10 (m, 2H), 4.23 (t, J=6.6 Hz, 2H), 4.14 (q, J=7.2 Hz, 2H), 3.74 (s, 2H), 3.29 (s, 2H), 3.26 (d, J=6.6 Hz, 2H), 2.97 (t, J=6.6 Hz, 2H), 2.53 (m, 1H), 2.36 (s, 3H), 1.96-1.28 (m, 10H), 1.25 (t, J=7.2 Hz, 3H).

EXAMPLE 1(5)

2-(N-allyl-N-(3-(2-(2-(4-(tetrahydropyran-4-yl)phenyl)-5-methyloxazol-4-yl)ethoxy)benzyl)amino)acetic acid ethyl ester

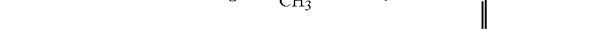

TLC: Rf 0.20 (hexane:ethyl acetate=2:1);

NMR (CDCl$_3$): δ 7.96-7.88 (m, 2H), 7.34-7.24 (m, 2H), 7.20 (dd, J=8.1, 8.1 Hz, 1H), 6.96-6.86 (m, 2H), 6.79 (m, 1H), 5.87 (ddt, J=17.1, 10.2, 6.6 Hz, 1H), 5.28-5.10 (m, 2H), 4.23 (t, J=6.6 Hz, 2H), 4.20-4.04 (m, 4H), 3.74 (s, 2H), 3.60-3.48 (m, 2H), 3.30 (s, 2H), 3.26 (d, J=6.6 Hz, 2H), 2.97 (t, J=6.6 Hz, 2H), 2.79 (m, 1H), 2.37 (s, 3H), 1.94-1.70 (m, 4H), 1.25 (t, J=7.2 Hz, 3H).

EXAMPLE 1(6)

2-(N-allyl-N-(3-(2-(5-methyl-2-piperidinothiazol-4-yl)ethoxy)benzyl)amino)acetic acid ethyl ester

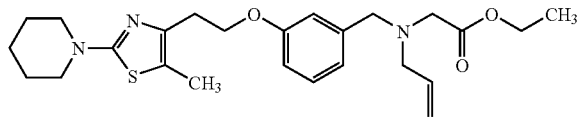

NMR (CDCl$_3$): δ 7.19 (t, J=8.1 Hz, 1H), 6.92-6.87 (m, 2H), 6.69 (m, 1H), 5.87 (m, 1H), 5.26-5.12 (m, 2H), 4.19 (t, J=7.2 Hz, 2H), 4.14 (q, J=7.2 Hz, 2H), 3.75 (s, 2H), 3.40-3.32 (m, 4H), 3.30 (s, 2H), 3.27 (d, J=6.3 Hz, 2H), 2.94 (t, J=7.2 Hz, 2H), 1.71-1.54 (m, 6H), 1.26 (t, J=7.2 Hz, 3H).

EXAMPLE 1(7)

2-(N-allyl-N-(3-(2-(2-phenyl-5-methyloxazol-4-yl)ethoxy)benzyl)amino)acetic acid ethyl ester

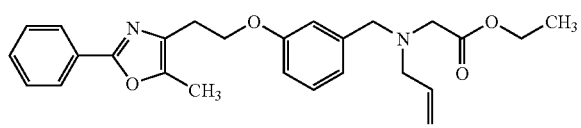

TLC: Rf 0.46 (hexane:ethyl acetate=2:1);

NMR (CDCl$_3$): δ 8.03-7.93 (m, 2H), 7.49-7.36 (m, 3H), 7.20 (dd, J=7.8, 7.8 Hz, 1H), 6.96-6.87 (m, 2H), 6.80 (m, 1H), 5.87 (m, 1H), 5.28-5.10 (m, 2H), 4.24 (t, J=6.8 Hz, 2H), 4.14 (q, J=7.0 Hz, 2H), 3.75 (s, 2H), 3.30 (s, 2H), 3.28 (m, 2H), 2.98 (t, J=6.8 Hz, 2H), 2.38 (s, 3H), 1.25 (t, J=7.0 Hz, 3H).

EXAMPLE 1(8)

2-(N-allyl-N-(3-(2-(2-(6-dimethylaminopyridin-3-yl)-5-methyloxazol-4-yl)ethoxy)benzyl)amino)acetic acid ethyl ester

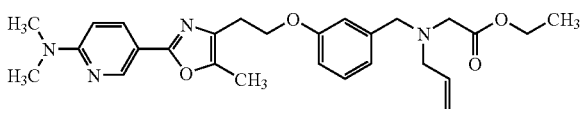

TLC: Rf 0.28 (hexane:ethyl acetate=2:1);

NMR (CDCl$_3$): δ 8.74 (m, 1H), 7.99 (dd, J=9.0, 2.4 Hz, 1H), 7.20 (dd, J=8.0, 8.0 Hz, 1H), 6.94-6.86 (m, 2H), 6.79 (m, 1H), 6.53 (m, 1H), 5.87 (ddt, J=16.8, 10.0, 6.5 Hz, 1H), 5.21 (m, 1H), 5.14 (m, 1H), 4.22 (t, J=7.0 Hz, 2H), 4.14 (q, J=7.0 Hz, 2H), 3.75 (s, 2H), 3.30 (s, 2H), 3.27 (d, J=6.5 Hz, 2H), 3.14 (s, 6H), 2.95 (t, J=7.0 Hz, 2H), 2.34 (s, 3H), 1.25 (t, J=7.0 Hz, 3H).

EXAMPLE 1(9)

2-(N-allyl-N-(3-(2-(2-(4-di methylaminophenyl)-5-methyloxazol-4-yl)ethoxy)benzyl)amino)acetic acid ethyl ester

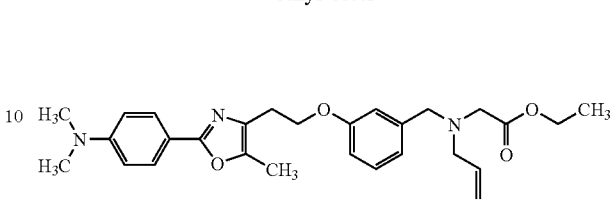

TLC: Rf 0.26 (hexane:ethyl acetate=4:1).

EXAMPLE 1(10)

2-(N-allyl-N-(3-(2-(5-methyl-2-phenyloxazol-4-yl)ethoxy)benzyl)amino)-2-methylpropionic acid methyl ester

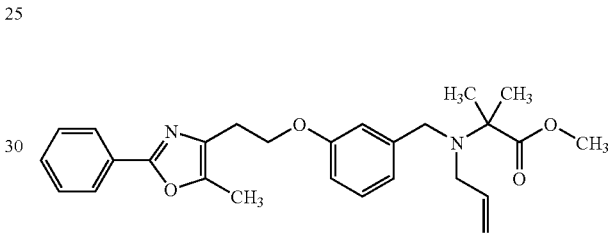

TLC: Rf 0.48 (hexane:ethyl acetate=4:1);

NMR (CDCl$_3$): δ 8.02-7.94 (m, 2H), 7.48-7.37 (m, 3H), 7.17 (dd, J=8.0, 8.0 Hz, 1H), 6.98-6.88 (m, 2H), 6.73 (m, 1H), 5.78 (ddt, J=16.5, 10.0, 6.5 Hz, 1H), 5.00 (m, 1H), 4.90 (m, 1H), 4.24 (t, J=6.5 Hz, 2H), 3.77 (s, 2H), 3.69 (s, 3H), 3.28 (d, J=6.5 Hz, 2H), 2.98 (t, J=6.5 Hz, 2H), 2.38 (s, 3H), 1.38 (s, 6H).

EXAMPLE 1(11)

2-(N-allyl-N-(3-(2-(2-(6-morpholinopyridin-3-yl)-5-methyloxazol-4-yl)ethoxy)benzyl)amino)acetic acid ethyl ester

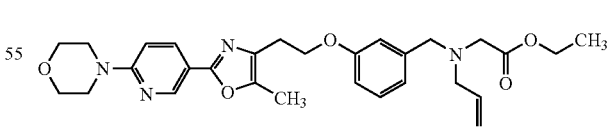

TLC: Rf 0.44 (chloroform:methanol=10:1);

NMR (CDCl$_3$): δ 8.76 (d, J=2.4 Hz, 1H), 8.04 (dd, J=9.0, 2.4 Hz, 1H), 7.19 (t, J=9.2 Hz, 1H), 6.96-6.85 (m, 2H), 6.83-6.74 (m, 1H), 6.64 (d, J=9.0 Hz, 1H), 5.98-5.74 (m, 1H), 5.27-5.04 (m, 2H), 4.28-4.06 (m, 4H), 3.87-3.78 (m, 4H), 3.74 (s, 2H), 3.65-3.55 (m, 4H), 3.32-3.22 (m, 4H), 2.95 (t, J=7.0 Hz, 2H), 2.35 (s, 3H), 1.25 (m, 3H).

EXAMPLE 1(12)

2-(N-allyl-N-(3-(2-(2-(6-piperidinopyridin-3-yl)-5-methyloxazol-4-yl)ethoxy)benzyl)amino)acetic acid ethyl ester

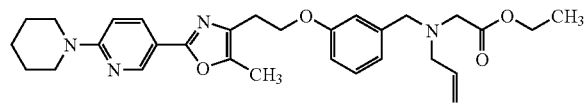

TLC: Rf 0.33 (chloroform:methanol=10:1);
NMR (CDCl$_3$): δ 8.72 (d, J=2.4 Hz, 1H), 7.97 (dd, J=9.0, 2.4 Hz, 1H), 7.19 (t, J=8.0 Hz, 1H), 6.96-6.85 (m, 2H), 6.79 (m, 1H), 6.64 (d, J=9.0 Hz, 1H), 5.98-5.73 (m, 1H), 5.27-5.04 (m, 2H), 4.28-4.03 (m, 4H), 3.74 (s, 2H), 3.61 (brs, 4H), 3.32-3.22 (m, 4H), 2.94 (t, J=6.6 Hz, 2H), 2.34 (s, 3H), 1.65 (brs, 6H), 1.25 (m, 3H).

EXAMPLE 1(13)

2-(N-allyl-N-(3-(2-(2-(6-diethylaminopyridin-3-yl)-5-methyloxazol-4-yl)ethoxy)benzyl)amino)acetic acid ethyl ester

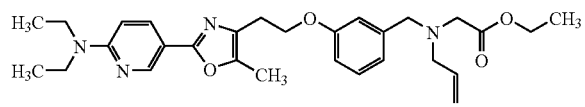

TLC: Rf 0.48 (chloroform:methanol=10:1);
NMR (CDCl$_3$): δ 8.71 (d, J=2.6 Hz, 1H), 7.95 (dd, J=9.2, 2.6 Hz, 1H), 7.19 (t, J=6.8 Hz, 1H), 6.95-6.75 (m, 3H), 6.47 (d, J=9.2 Hz, 1H), 5.85 (m, 1H), 5.21 (d, J=17.2 Hz, 1H), 5.14 (d, J=10.3 Hz, 1H), 4.22 (t, J=6.8 Hz, 2H), 4.14 (q, J=7.2 Hz, 2H), 3.74 (s, 2H), 3.55 (q, J=7.0 Hz, 4H), 3.29 (s, 2H), 3.27 (d, J=6.4 Hz, 2H), 2.91 (t, J=6.8 Hz, 2H), 2.34 (s, 3H), 1.35-1.15 (m, 9H).

EXAMPLE 1(14)

2-(N-allyl-N-(3-(2-(2-(6-pyrrolidinopyridin-3-yl)-5-methyloxazol-4-yl)ethoxy)benzyl)amino)acetic acid ethyl ester

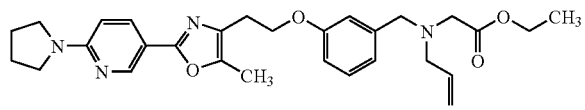

TLC: Rf 0.80 (chloroform:methanol=10:1);
NMR (CDCl$_3$): δ 8.73 (d, J=2.4 Hz, 1H), 7.98 (dd, J=8.8, 2.4 Hz, 1H), 7.19 (t, J=7.2 Hz, 1H), 6.93-6.75 (m, 2H), 6.91 (s, 1H), 6.37 (d, J=8.8 Hz, 1H), 5.98-5.74 (m, 1H), 5.29-5.09 (m, 2H), 4.22 (t, J=6.6 Hz, 2H), 4.16 (q, J=7.2 Hz, 2H), 3.74 (s, 2H), 3.50 (m, 4H), 3.29 (s, 2H), 3.26 (d, J=6.6 Hz, 2H), 2.94 (t, J=6.6 Hz, 2H), 2.34 (s, 3H), 2.02 (m, 4H), 1.24 (t, J=7.2 Hz, 3H).

EXAMPLE 1(15)

2-(N-allyl-N-(3-(2-(2-(4-morpholinophenyl)-5-methyloxazol-4-yl)ethoxy)benzyl)amino)acetic acid ethyl ester

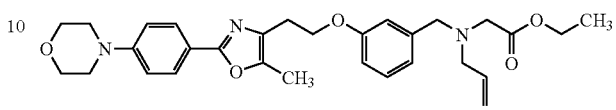

NMR (CDCl$_3$): δ 7.87 (d, J=9.0 Hz, 2H), 7.20 (t, J=8.1 Hz, 1H), 6.95-6.87 (m, 4H), 6.79 (m, 1H), 5.86 (m, 1H), 5.25-5.11 (m, 2H), 4.23 (t, J=6.6 Hz, 2H), 4.14 (q, J=6.9 Hz, 2H), 3.87 (t, J=4.5 Hz, 4H), 3.74 (s, 2H), 3.32-3.20 (m, 8H), 2.96 (t, J=6.6 Hz, 2H), 2.35 (s, 3H), 1.25 (t, J=6.9 Hz, 3H).

EXAMPLE 1(16)

2-(N-allyl-N-(3-(2-(2-morpholino-5-methylthiazol-4-yl)ethoxy)benzyl)amino)acetic acid t-butyl ester

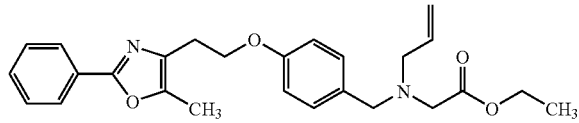

TLC: Rf 0.85 (chloroform:methanol=9:1);
NMR (CDCl$_3$): δ 7.19 (t, J=8.4 Hz, 1H), 6.94-6.87 (m, 2H), 6.77 (m, 1H), 5.86 (m, 1H), 5.26-5.10 (m, 2H), 4.19 (t, J=6.9 hz, 2H), 3.79 (t, J=4.5 Hz, 4H), 3.75 (s, 2H), 3.37 (t, J=4.5 Hz, 4H), 3.26 (d, J=6.6 Hz, 2H), 3.21 (s, 2H), 2.95 (t, J=6.9 Hz, 2H), 2.05 (s, 3H), 1.46 (s, 9H).

EXAMPLE 1(17)

2-(N-allyl-N-(4-(2-(5-methyl-2-phenyloxazol-4-yl)ethoxy)benzyl)amino)acetic acid ethyl ester TLC: Rf 0.64 (hexane:ethyl acetate=1:1);
NMR (CDCl$_3$): δ 8.00-7.95 (m, 2H), 7.44-7.39 (m, 3H), 7.23 (d, J=8.7 Hz, 2H), 6.85 (d, J=8.7 Hz, 2H), 5.94-5.80 (m, 1H), 5.23-5.11 (m, 2H), 4.23 (t, J=6.6 Hz, 2H), 4.14 (q, J=7.2 Hz, 2H), 3.70 (s, 2H), 3.27 (s, 2H), 3.24 (d, J=6.6 Hz, 2H), 2.97 (t, J=6.6 Hz, 2H), 2.37 (s, 3H), 1.25 (t, J=7.2 Hz, 3H).

EXAMPLE 2

2-(N-allyl-N-(3-(2-(2-(6-(perhydroazepin-1-yl)pyridin-3-yl)-5-methyloxazol-4-yl)ethoxy)benzyl)amino)acetic acid

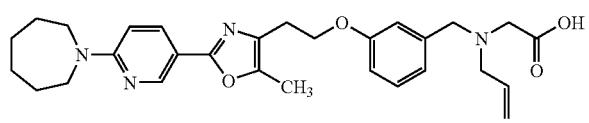

To a solution of the compound prepared in Example 1 (777 mg) in ethanol and tetrahydrofuran (20 mL, 1:1) was added 2N aqueous sodium hydroxide solution (3.0 mL) at room temperature and the mixture was stirred for 15 hours. The reaction mixture was adjusted to about pH 5 with 2N hydrochloric acid and extracted with ethyl acetate. The extract was washed with water and brine sequentially, dried over anhydrous magnesium sulfate and concentrated to give the compound of the present invention (546 mg) having the following physical data.

TLC: Rf 0.18 (chloroform:methanol=9:1);
NMR (CDCl$_3$): δ 8.71 (d, J=2.4 Hz, 1H), 7.96 (dd, J=9.0, 2.4 Hz, 1H), 7.24 (dd, J=7.8, 7.5 Hz, 1H), 6.93-6.82 (m, 3H), 6.51 (d, J=9.0 Hz, 1H), 5.96-5.80 (m, 1H), 5.35-5.26 (m, 2H), 4.23 (t, J=6.9 Hz, 2H), 3.81 (s, 2H), 3.67 (dd, J=6.0, 6.0 Hz, 4H), 3.34 (d, J=6.9 Hz, 2H), 3.29 (s, 2H), 3.00-2.70 (br, 1H), 2.94 (t, J=6.9 Hz, 2H), 2.34 (s, 3H), 1.84-1.72 (m, 4H), 1.59-1.50 (m, 4H).

EXAMPLE 2(1) TO EXAMPLE 2(17)

By the same procedure as described in Example 2 using the compounds prepared in Example 1(1)-Example 1(17) instead of the compound prepared in Example 1 and, if necessary, followed by converting to a corresponding salt with the conventional method, the following compounds of the present invention were obtained.

EXAMPLE 2(1)

2-(N-allyl-N-(3-(2-(2-isopropyl-5-methyloxazol-4-yl)ethoxy)benzyl)amino)acetic acid

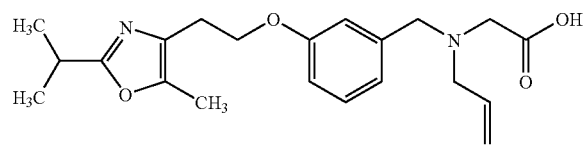

TLC: Rf 0.32 (chloroform:methanol: acetic acid=100:10:1);
NMR (CDCl$_3$): δ 7.20 (dd, J=8.0, 8.0 Hz, 1H), 6.94-6.78 (m, 3H), 5.92 (m, 1H), 5.30 (d, J=11.4 Hz, 1H), 5.29 (d, J=15.0 Hz, 1H), 4.15 (t, J=7.0 Hz, 2H), 3.88 (s, 2H), 3.38 (d, J=7.0 Hz, 2H), 3.31 (s, 2H), 2.99 (sept, J=7.0 Hz, 1H), 2.86 (t, J=7.0 Hz, 2H), 2.24 (s, 3H), 1.30 (d, J=7.0 Hz, 6H).

EXAMPLE 2(2)

2-(N-allyl-N-(3-(2-(2-(4-methylpiperazin-1-yl)-5-methylthiazol-4-yl)ethoxy)benzyl)amino)acetic acid

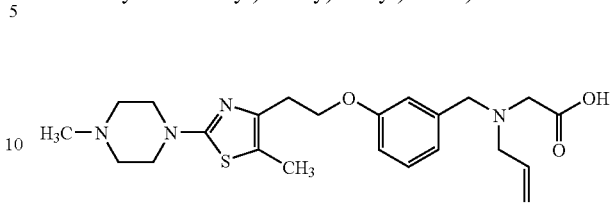

TLC: Rf 0.69 (chloroform:methanol: water=50:20:1);
NMR (CDCl$_3$): δ 7.20 (dd, J=8.0, 8.0 Hz, 1H), 6.95-6.87 (m, 2H), 6.81 (dd, J=8.0, 2.0 Hz, 1H), 5.93 (m, 1H), 5.28 (d, J=16.8 Hz, 1H), 5.27 (d, J=10.5 Hz, 1H), 4.19 (t, J=7.0 Hz, 2H), 3.88 (s, 2H), 3.45 (dd, J=5.0, 5.0 Hz, 4H), 3.38 (d, J=6.5 Hz, 2H), 3.31 (s, 2H), 2.92 (t, J=7.0 Hz, 2H), 2.59 (dd, J=5.0, 5.0 Hz, 4H), 2.37 (s, 3H), 2.24 (s, 3H).

EXAMPLE 2(3)

2-(N-allyl-N-(3-(2-(2-(4-(1,2,3-thiadiazol-4-yl)phenyl)-5-methyloxazol-4-yl)ethoxy)benzyl)amino)acetic acid sodium salt

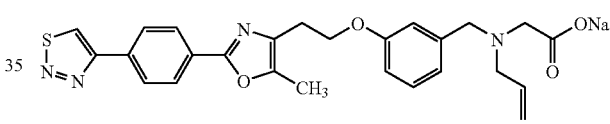

TLC: Rf 0.36 (chloroform:methanol=8:1);
NMR (DMSO-d$_6$): δ 9.74 (s, 1H), 8.28 (d, J=8.6 Hz, 2H), 8.07 (d, J=8.6 Hz, 2H), 7.16 (dd, J=7.8, 7.8 Hz, 1H), 6.95-6.70 (m, 3H), 5.80 (m, 1H), 5.19-4.96 (m, 2H), 4.20 (t, J=6.5 Hz, 2H), 3.67 (s, 2H), 3.19 (d, J=6.0 Hz, 2H), 2.94 (t, J=6.5 Hz, 2H), 2.77 (s, 2H), 2.38 (s, 3H).

EXAMPLE 2(4)

2-(N-allyl-N-(3-(2-(2-(4-cyclohexylphenyl)-5-methyloxazol-4-yl)ethoxy)benzyl)amino)acetic acid

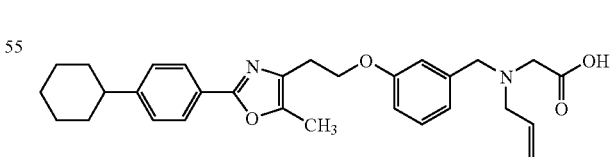

TLC: Rf 0.32 (chloroform:methanol=8:1);
NMR (CDCl$_3$): δ 7.86 (d, J=8.4 Hz, 2H), 7.30-7.18 (m, 3H), 7.12-7.00 (m, 2H), 6.88 (m, 1H), 6.03 (m, 1H), 5.56 (brs, 1H), 5.48-5.30 (m, 2H), 4.36-4.04 (m, 4H), 3.68 (d, J 6.3 Hz, 2H), 3.52 (s, 2H), 2.93 (t, J=6.6 Hz, 2H), 2.51 (m, 1H), 2.34 (s, 3H), 1.96-1.68 (m, 5H), 1.52-1.14 (m, 5H).

EXAMPLE 2(5)

2-(N-allyl-N-(3-(2-(2-(4-(tetrahydropyran-4-yl)phenyl)-5-methyloxazol-4-yl)ethoxy)benzyl)amino)acetic acid

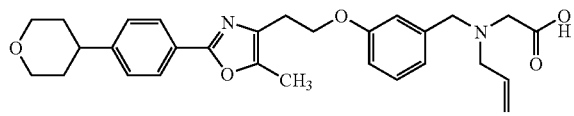

TLC: Rf 0.39 (chloroform:methanol=4:1);
NMR (CDCl$_3$): δ 7.91 (d, J=8.1 Hz, 2H), 7.36-7.24 (m, 3H), 7.16 (m, 1H), 7.05 (m, 1H), 6.92 (m, 1H), 6.14 (m, 1H), 5.54-5.38 (m, 2H), 5.08 (brs, 1H), 4.34-4.02 (m, 6H), 3.76 (d, J=6.3 Hz, 2H), 3.62-3.54 (m, 4H), 2.94 (t, J=6.6 Hz, 2H), 2.80 (m, 1H), 2.38 (s, 3H), 1.92-1.70 (m, 4H).

EXAMPLE 2(6)

2-(N-allyl-N-(3-(2-(5-methyl-2-piperidinothiazol-4-yl)ethoxy)benzyl)amino)acetic acid ½ calcium salt

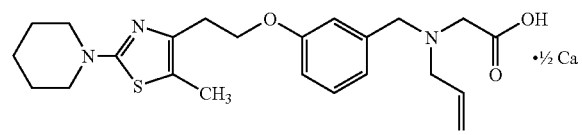

TLC: 0.55 (chloroform:methanol=5:1);
NMR (CDCl$_3$): δ 7.13 (t, J=8.1 Hz, 1H), 6.89-6.80 (m, 2H), 6.72 (m, 1H), 5.80 (m, 1H), 5.16-4.98 (m, 2H), 4.09 (t, J=6.9 Hz, 2H), 3.67 (s, 2H), 3.36-3.12 (m, 6H), 2.92 (s, 2H), 2.80 (t, J=6.9 Hz, 2H), 2.16 (s, 3H), 1.58-1.48 (m, 6H).

EXAMPLE 2(7)

2-(N-allyl-N-(3-(2-(5-methyl-2-phenyloxazol-4-yl)ethoxy)benzyl)amino)acetic acid

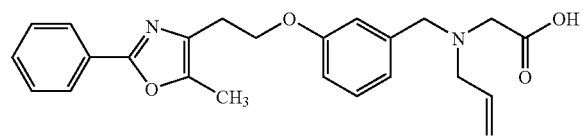

Free Form
TLC: Rf 0.21 (chloroform:methanol=8:1);
NMR (CDCl$_3$): δ 8.02-7.90 (m, 2H), 7.48-7.35 (m, 3H), 7.23 (m, 1H), 7.05-6.83 (m, 3H), 5.96 (m, 1H), 5.44-5.28 (m, 2H), 4.22 (t, J=6.6 Hz, 2H), 4.12 (s, 2H), 3.60 (m, 2H), 3.47 (s, 2H), 2.94 (t, J=6.6 Hz, 2H), 2.35 (s, 3H).

Sodium Salt
TLC: Rf 0.61 (chloroform:methanol=4:1);
NMR (DMSO-d$_6$): δ 7.95-7.90 (m, 2H), 7.55-7.45 (m, 3H), 7.15 (dd, J=8, 8 Hz, 1H), 6.95-6.70 (m, 3H), 5.80 (m, 1H), 5.20-5.00 (m, 2H), 4.20 (t, J=6.5 Hz, 2H), 3.70 (s, 2H), 3.20 (d, J=7 Hz, 2H), 2.95 (t, J=6.5 Hz, 2H), 2.80 (s, 2H), 2.35 (s, 3H).

EXAMPLE 2(8)

2-(N-allyl-N-(3-(2-(2-(6-dimethylaminopyridin-3-yl)-5-methyloxazol-4-yl)ethoxy)benzyl)amino)acetic acid

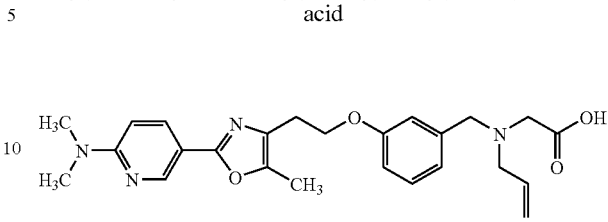

TLC: Rf 0.26 (chloroform:methanol: acetic acid=100:10:1);
NMR (CDCl$_3$): δ 8.73 (d, J=2.4 Hz, 1H), 7.99 (dd, J=2.4, 9.0, 1.5 Hz, 1H), 7.24 (dd, J=8.0, 8.0 Hz, 1H), 6.94-6.81 (m, 3H), 6.52 (d, J=9.0 Hz, 1H), 5.90 (m, 1H), 5.31 (d, J=11.2 Hz, 1H), 5.30 (d, J=15.8 Hz, 1H), 4.22 (t, J=7.0 Hz, 2H), 3.85 (s, 2H), 3.36 (d, J=7.0 Hz, 2H), 3.31 (s, 2H), 3.14 (s, 6H), 2.93 (t, J=7.0 Hz, 2H), 2.34 (s, 3H).

EXAMPLE 2(9)

2-(N-allyl-N-(3-(2-(2-(4-dimethylaminophenyl)-5-methyloxazol-4-yl)ethoxy)benzyl)amino)acetic acid

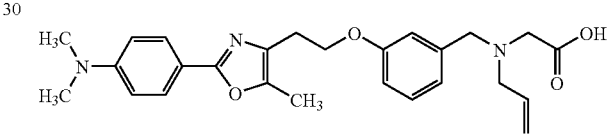

TLC: Rf 0.31 (chloroform:methanol: acetic acid=100:10:1);
NMR (CDCl$_3$): δ 7.83 (m, 2H), 7.22 (dd, J=8.0, 8.0 Hz, 1H), 6.94-6.80 (m, 3H), 6.70 (m, 2H), 5.89 (m, 1H), 5.29 (d, J=11.8 Hz, 1H), 5.28 (d, J=15.2 Hz, 1H), 4.22 (t, J=7.0 Hz, 2H), 3.84 (s, 2H), 3.35 (d, J=7.0 Hz, 2H), 3.29 (s, 2H), 3.00 (s, 6H), 2.93 (t, J=7.0 Hz, 2H), 2.32 (s, 3H).

EXAMPLE 2(10)

2-(N-allyl-N-(3-(2-(2-phenyl-5-methyloxazol-4-yl)ethoxy)benzyl)amino)-2-methylpropionic acid

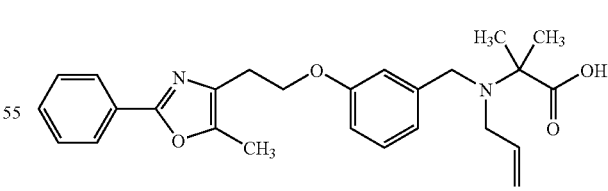

Free Form
TLC: Rf 0.32 (chloroform:methanol=10:1);
NMR (CDCl$_3$): δ 8.02-7.95 (m, 2H), 7.47-7.39 (m, 3H), 7.25 (m, 1H), 6.96-6.89 (m, 2H), 6.85 (m, 1H), 5.85 (ddt, J=16.8, 10.2, 6.6 Hz, 1H), 5.21 (m, 1H), 5.18 (m, 1H), 4.25 (t, J=7.0 Hz, 2H), 3.74 (s, 2H), 3.32 (d, J=6.6 Hz, 2H), 2.98 (t, J=7.0 Hz, 2H), 2.38 (s, 3H), 1.45 (s, 6H).

Sodium Salt

TLC: Rf 0.42 (chloroform:methanol=10:1);

NMR (DMSO-$d_6$): δ 7.96-7.86 (m, 2H), 7.56-7.43 (m, 3H), 7.12 (dd, J=8.0, 8.0 Hz, 1H), 6.99 (brs, 1H), 6.89 (d, J=8.0 Hz, 1H), 6.69 (dd, J=8.0, 2.0 Hz, 1H), 5.75 (ddt, J=17.0, 10.5, 6.0 Hz, 1H), 4.92 (m, 1H), 4.76 (m, 1H), 4.18 (t, J=7.0 Hz, 2H), 3.76 (s, 2H), 3.29 (d, J=6.0 Hz, 2H), 2.92 (t, J=7.0 Hz, 2H), 2.36 (s, 3H), 1.17 (s, 6H).

EXAMPLE 2(11)

2-(N-allyl-N-(3-(2-(2-(6-morpholinopyridin-3-yl)-5-methyloxazol-4-yl)ethoxy)benzyl)amino)acetic acid

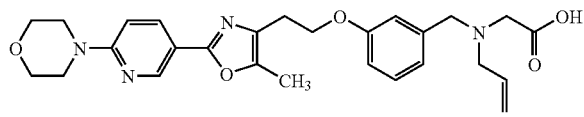

TLC: Rf 0.22 (chloroform:methanol=10:1);

NMR (CDCl$_3$): δ 8.76 (d, J=2.2 Hz, 1H), 8.04 (dd, J=9.0, 2.2 Hz, 1H), 7.24 (t, J=8.0 Hz, 1H), 6.96-6.82 (m, 3H), 6.64 (d, J=9.0 Hz, 1H), 6.01-5.78 (m, 1H), 5.32 (d, J=10.8 Hz, 1H), 5.31 (d, J=15.4 Hz, 1H), 4.22 (t, J=6.8 Hz, 2H), 3.84 (s, 2H), 3.82 (t, J=5.0 Hz, 4H), 3.59 (t, J=5.0 Hz, 4H), 3.37 (d, J=6.8 Hz, 2H), 3.31 (s, 2H), 2.94 (t, J=6.8 Hz, 2H), 2.35 (s, 3H).

EXAMPLE 2(12)

2-(N-allyl-N-(3-(2-(2-(6-piperidinopyridin-3-yl)-5-methyloxazol-4-yl)ethoxy)benzyl)amino)acetic acid

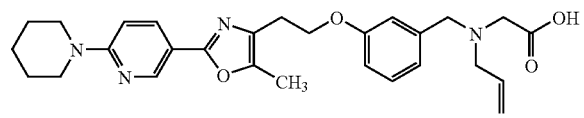

TLC: Rf 0.28 (chloroform:methanol=10:1);

NMR (CDCl$_3$): δ 8.72 (d, J=2.2 Hz, 1H), 7.97 (dd, J=9.0, 2.2 Hz, 1H), 7.23 (t, J=8.0 Hz, 1H), 6.97-6.79 (m, 3H), 6.64 (d, J=9.0 Hz, 1H), 6.02-5.77 (m, 1H), 5.31 (d, J=9.8 Hz, 1H), 5.29 (d, J=16.0 Hz, 1H), 4.21 (t, J=6.8 Hz, 2H), 3.85 (s, 2H), 3.60 (br s, 4H), 3.36 (d, J=7.0 Hz, 2H), 3.30 (s, 2H), 2.92 (t, J=6.8 Hz, 2H), 2.33 (s, 3H), 1.65 (br s, 6H).

EXAMPLE 2(13)

2-(N-allyl-N-(3-(2-(2-(6-diethylaminopyridin-3-yl)-5-methyloxazol-4-yl)ethoxy)benzyl)amino)acetic acid

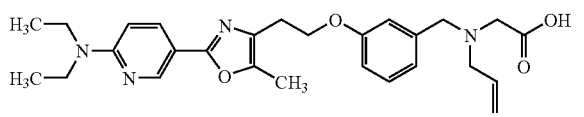

TLC: Rf 0.22 (chloroform:methanol=10:1);

NMR (CDCl$_3$): δ 8.71 (d, J=2.4 Hz, 1H), 7.95 (dd, J=9.0, 2.4 Hz, 1H), 7.23 (t, J=7.8 Hz, 1H), 6.97-6.81 (m, 3H), 6.47 (d, J=9.0 Hz, 1H), 6.00-5.78 (m, 1H), 5.31 (d, J=10.8 Hz, 1H), 5.30 (d, J=15.8 Hz, 1H), 4.22 (t, J=7.0 Hz, 2H), 3.84 (s, 2H), 3.55 (q, J=7.2 Hz, 4H), 3.36 (d, J=7.4 Hz, 2H), 3.30 (s, 2H), 2.93 (t, J=7.0 Hz, 2H), 2.33 (s, 3H), 1.99 (t, J=7.2 Hz, 6H).

EXAMPLE 2(14)

2-(N-allyl-N-(3-(2-(2-(6-pyrrolidinopyridin-3-yl)-5-methyloxazol-4-yl)ethoxy)benzyl)amino)acetic acid

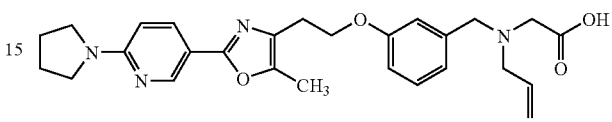

TLC: Rf 0.49 (chloroform:methanol=6:1);

NMR (CDCl$_3$): δ 8.73 (d, J=2.2 Hz, 1H), 7.98 (dd, J=8.8, 2.2 Hz, 1H), 7.23 (t, J=8.0 Hz, 1H), 6.97-6.81 (m, 3H), 6.38 (d, J=8.8 Hz, 1H), 6.04-5.77 (m, 1H), 5.30 (d, J=10.4 Hz, 1H), 5.29 (d, J=15.6 Hz, 1H), 4.22 (t, J=7.0 Hz, 2H), 3.80 (s, 2H), 3.50 (m, 4H), 3.33 (d, J=6.6 Hz, 2H), 3.28 (s, 2H), 2.93 (t, J=7.0 Hz, 2H), 2.34 (s, 3H), 2.02 (m, 4H).

EXAMPLE 2(15)

2-(N-allyl-N-(3-(2-(2-(4-morpholinophenyl)-5-methyloxazol-4-yl)ethoxy)benzyl)amino)acetic acid hydrochloride

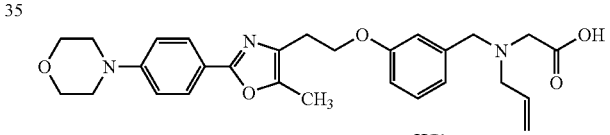

TLC: Rf 0.25 (chloroform:methanol=9:1);

NMR (DMSO-$d_6$): δ 7.74 (d, J=9.0 Hz, 2H), 7.20 (t, J=8.1 Hz, 1H), 7.01 (d, J=9.0 Hz, 2H), 6.91-6.77 (m, 3H), 5.81 (m, 1H), 5.22-5.09 (m, 2H), 4.17 (t, J=6.3 Hz, 2H), 3.73 (t, J=4.2 Hz, 4H), 3.68 (s, 2H); 3.52-3.08 (m, 9H), 2.87 (t, J=6.3 Hz, 2H), 2.31 (s, 3H).

EXAMPLE 2(16)

2-(N-allyl-N-(3-(2-(5-methyl-2-morpholinothiazol-4-yl)ethoxy)benzyl)amino)acetic acid dihydrochloride

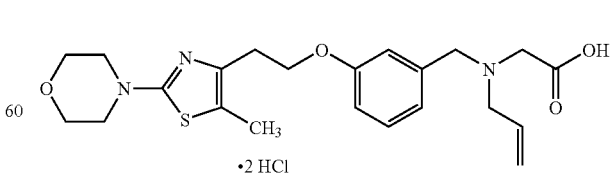

TLC: Rf 0.28 (chloroform:methanol=9:1);

NMR (DMSO-$d_6$): δ 10.96 (br, 1H), 7.34 (t, J=8.1 Hz, 1H), 7.24 (m, 1H), 7.09 (d, J=8.1 Hz, 1H), 6.99 (dd, J=8.1, 2.1 Hz, 1H), 6.03 (m, 1H), 5.56-5.47 (m, 2H), 4.35 (s, 2H), 4.24 (t, J=6.3 Hz, 2H), 3.89 (s, 2H), 3.82 (d, J=6.9 Hz, 2H), 3.76-3.54 (m, 8H), 3.07 (t, J=6.3 Hz, 2H), 2.34 (s, 3H).

EXAMPLE 2(17)

2-(N-allyl-N-(4-(2-(5-methyl-2-phenyloxazol-4-yl)ethoxy)benzyl)amino)acetic acid

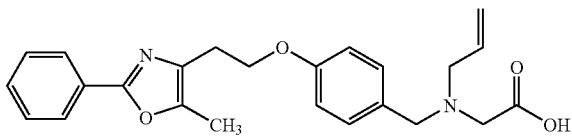

TLC: Rf 0.14 (chloroform:methanol=9:1);
NMR (CDCl$_3$): δ 8.00-7.95 (m, 2H), 7.43-7.39 (m, 3H), 7.23 (d, J=8.4 Hz, 2H), 6.89 (d, J=8.4 Hz, 2H), 5.95-5.80 (m, 1H), 5.37-5.28 (m, 2H), 4.24 (t, J=6.6 Hz, 2H), 3.84 (s, 2H), 3.35 (d, J=7.2 Hz, 2H), 3.29 (s, 2H), 2.98 (t, J=6.6 Hz, 2H), 2.60-2.20 (brs, 1H), 2.38 (s, 3H).

PREPARATION EXAMPLE 1

The following components were admixed in a conventional method, punched out to give 100 tablets each containing 50 mg of active ingredient.

| | |
|---|---|
| 2-(N-allyl-N-(3-(2-(2-(6-(perhydroazepin-1-yl)pyridin-3-yl)-5-methyloxazol-4-yl)ethoxy)benzyl)amino)acetic acid | 5.0 g |
| calcium carboxymethylcellulose (disintegrant) | 0.2 g |
| magnesium stearate (lubricant) | 0.1 g |
| microcrystalline cellulose | 4.7 g |

PREPARATION EXAMPLE 2

After mixing the following components by a conventional method, the resulting solution was sterilized by a conventional method and 5 ml portions thereof were filled in amples, respectively, and freeze-dried by a conventional method to obtain 100 amples of injection containing each 20 mg of the active ingredient.

| | |
|---|---|
| 2-(N-allyl-N-(3-(2-(2-(6-(perhydroazepin-1-yl)pyridin-3-yl)-5-methyloxazol-4-yl)ethoxy)benzyl)amino)acetic acid | 2.0 g |
| Mannitol | 20 g |
| Distilled water | 1000 ml |

---

The invention claimed is:

1. A carboxylic acid derivative compound represented by formula (I)

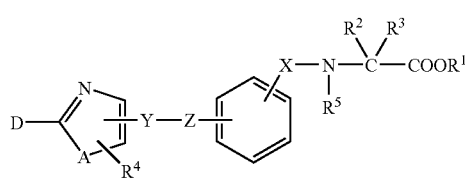

wherein X and Y are each independently $C_{1-4}$ alkylene,
Z is —O— or —S—,
$R^1$, $R^2$, $R^3$ and $R^4$ are each independently hydrogen atom, or $C_{1-8}$ alkyl,
$R^5$ is $C_{2-8}$ alkenyl,
A is —O— or —S—,
D is

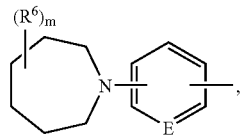

$R^6$ is (1) hydrogen atom,
(2) $C_{1-8}$ alkyl,
(3) $C_{1-8}$ alkoxy,
(4) $CF_3$,
(5) $OCF_3$,
(6) halogen atom,
(7) nitro, or
(8) $NR^7R^8$,
$R^7$ or $R^8$ is hydrogen atom, or $C_{1-8}$ alkyl, or
$R^7$ and $R^8$, taken together with the nitrogen atom to which they are attached, form saturated 3-7 membered monohetero aryl containing one nitrogen atom and optionally another one hetero atom selected from oxygen, sulfur and nitrogen atom, and the saturated hetero aryl is optionally substituted with $C_{1-8}$ alkyl,
E is CH or nitrogen atom, and
m is integer of 1-3, or
a nontoxic salt thereof.

2. The compound according to claim 1, wherein Z is —O— or a nontoxic salt thereof.

3. The compound according to claim 1, which is
(1) 2-(N-allyl-N-(3-(2-(2-(6-(perhydroazepin-1-yl)pyridin-3-yl)-5-methyloxazol-4-yl)ethoxy)benzyl)amino)acetic acid ethyl ester, or
(2) 2-(N-allyl-N-(3-(2-(2-(6-(perhydroazepin-1-yl)pyridin-3-yl)-5-methyloxazol-4-yl)ethoxy)benzyl)amino)acetic acid, or a nontoxic salt thereof.

4. A pharmaceutical composition comprising a therapeutically effective amount of a compound of claim 1 and a pharmaceutically acceptable carrier.

5. A method of treating hyperglycemia or hyperlipidemia in a subject in need thereof comprising administering to said subject a therapeutically effective amount of a compound of claim 1.

6. The method of claim 5 wherein the hyperglycemia causes syndrome X, obesity, hypertension or atherosclerosis.

7. The method of claim 5 wherein HDL cholesterol of said subject was elevated and/or LDL cholesterol or VLDL cholesterol was lowered.

* * * * *

SEQUENCE LISTING

<160> NUMBER OF SEQ ID NOS: 3

<210> SEQ ID NO 1
<211> LENGTH: 85
<212> TYPE: DNA
<213> ORGANISM: Artificial Sequence
<220> FEATURE:
<223> OTHER INFORMATION: Enhancer sequence including four times repeated
      Gal4 protein
      response sequences

<400> SEQUENCE: 1
tcgacggagt actgtcctcc gcgacggagt actgtcctcc gcgacggagt actgtcctcc    60
gcgacggagt actgtcctcc gagct                                         85

<210> SEQ ID NO 2
<211> LENGTH: 9
<212> TYPE: PRT
<213> ORGANISM: Simian virus 40

<400> SEQUENCE: 2

Ala Pro Lys Lys Lys Arg Lys Val Gly
1               5

<210> SEQ ID NO 3
<211> LENGTH: 9
<212> TYPE: PRT
<213> ORGANISM: Artificial Sequence
<220> FEATURE:
<223> OTHER INFORMATION: hemagglutinin epitope

```
<400> SEQUENCE: 3

Tyr Pro Tyr Asp Val Pro Asp Tyr Ala
1               5
```